(12) United States Patent
Guan et al.

(10) Patent No.: US 12,303,524 B2
(45) Date of Patent: **\*May 20, 2025**

(54) COMPOSITIONS COMPRISING S-ADENOSYLMETHIONINE AND A GALLIC ACID ESTER

(71) Applicant: MSI-195 HOLDINGS, LLC, Harrison, NY (US)

(72) Inventors: Dechi Guan, Vancouver (CA); I. David MacDonald, Surrey (GB)

(73) Assignee: MSI-195 HOLDINGS, LLC, Harrison, NY (US)

( \* ) Notice: Subject to any disclaimer, the term of this patent is extended or adjusted under 35 U.S.C. 154(b) by 32 days.

This patent is subject to a terminal disclaimer.

(21) Appl. No.: 17/688,679

(22) Filed: Mar. 7, 2022

(65) Prior Publication Data

US 2022/0193107 A1 Jun. 23, 2022

Related U.S. Application Data

(63) Continuation of application No. 16/727,610, filed on Dec. 26, 2019, now abandoned, which is a
(Continued)

(51) Int. Cl.
*A61K 31/7076* (2006.01)
*A61K 9/00* (2006.01)
(Continued)

(52) U.S. Cl.
CPC ........ *A61K 31/7076* (2013.01); *A61K 9/0053* (2013.01); *A61K 9/28* (2013.01);
(Continued)

(58) Field of Classification Search
None
See application file for complete search history.

(56) References Cited

U.S. PATENT DOCUMENTS 3,893,999 A 7/1975 Fiecchi
3,954,726 A 5/1976 Fiecchi
(Continued)

FOREIGN PATENT DOCUMENTS

CA 2298245 8/2000
CA 2364063 9/2000
(Continued)

OTHER PUBLICATIONS

U.S. Appl. No. 12/024,059 Final Office Action dated Jun. 5, 2012, Non-patent literature.
(Continued)

*Primary Examiner* — Bethany P Barham
*Assistant Examiner* — Barbara S Frazier
(74) *Attorney, Agent, or Firm* — Arnall Golden Gregory LLP

(57) ABSTRACT

Provided herein are compositions and formulations comprising S-adenosyl-L-methionine ("SAM-e" or "SAMe") and one or more gallic acid esters. Also provided herein are methods for improving the delivery of SAMe. Compositions and formulations provided herein increase SAMe plasma concentrations and area under the curve (AUC) values. Also provided herein are methods of treating a disease or disorder in a subject by administering compositions or formulations comprising exogenous SAMe and one or more gallic acid esters.

14 Claims, 5 Drawing Sheets

Related U.S. Application Data continuation of application No. 15/932,359, filed on Feb. 16, 2018, now abandoned, which is a continuation of application No. 14/628,623, filed on Feb. 23, 2015, now Pat. No. 9,925,208, which is a continuation of application No. 14/247,061, filed on Apr. 7, 2014, now Pat. No. 8,975,238, which is a continuation of application No. PCT/CA2013/000876, filed on Oct. 16, 2013.

(60) Provisional application No. 61/715,138, filed on Oct. 17, 2012.

(51) Int. Cl.

| | |
|---|---|
| A61K 9/28 | (2006.01) |
| A61K 31/235 | (2006.01) |
| A61K 47/14 | (2017.01) |
| A61P 1/16 | (2006.01) |
| A61P 25/00 | (2006.01) |
| A61P 25/24 | (2006.01) |
| A61P 25/28 | (2006.01) |
| A61P 35/00 | (2006.01) |
| A61K 9/20 | (2006.01) |
| A61K 9/48 | (2006.01) |

(52) U.S. Cl.
CPC ............ *A61K 31/235* (2013.01); *A61K 47/14* (2013.01); *A61P 1/16* (2018.01); *A61P 25/00* (2018.01); *A61P 25/24* (2018.01); *A61P 25/28* (2018.01); *A61P 35/00* (2018.01); *A61K 9/2054* (2013.01); *A61K 9/2059* (2013.01); *A61K 9/4866* (2013.01)

(56) References Cited

U.S. PATENT DOCUMENTS

| | | |
|---|---|---|
| 4,057,686 A | 11/1977 | Fiecchi |
| 4,389,393 A | 6/1983 | Schor et al. |
| 4,525,345 A | 6/1985 | Dunn et al. |
| 4,537,772 A | 8/1985 | Alexander et al. |
| 4,556,678 A | 12/1985 | Hsiao |
| 4,601,894 A | 7/1986 | Hanna et al. |
| 4,680,323 A | 7/1987 | Lowey |
| 4,687,757 A | 8/1987 | Parrott et al. |
| 4,692,337 A | 9/1987 | Ukigawa et al. |
| 4,695,591 A | 9/1987 | Hanna et al. |
| 4,756,911 A | 7/1988 | Drost et al. |
| 4,956,173 A | 9/1990 | Le Fur et al. |
| 4,968,509 A | 11/1990 | Radebaugh et al. |
| 5,073,380 A | 12/1991 | Babu et al. |
| 5,128,249 A | 7/1992 | Gennari |
| 5,137,712 A | 8/1992 | Kask et al. |
| 5,169,642 A | 12/1992 | Brinker et al. |
| 5,264,446 A | 11/1993 | Hegasy et al. |
| 5,439,687 A | 8/1995 | Compassi |
| 5,462,747 A | 10/1995 | Radebaugh et al. |
| 5,543,154 A | 8/1996 | Rork et al. |
| 5,753,213 A | 5/1998 | Moratti |
| 5,877,935 A | 3/1999 | Sato et al. |
| 5,922,341 A | 7/1999 | Smith et al. |
| 5,962,522 A | 10/1999 | Wacher et al. |
| 6,004,575 A | 12/1999 | Luessen et al. |
| 6,093,703 A | 7/2000 | La Greca |
| 6,180,666 B1 | 1/2001 | Wacher et al. |
| 6,365,185 B1 | 4/2002 | Ritschel et al. |
| 6,548,555 B1 | 4/2003 | Curatolo |
| 6,555,124 B1 | 4/2003 | Kolter |
| 6,596,701 B1 | 7/2003 | Schwartz et al. |
| 6,635,615 B1 | 10/2003 | Hebert |
| 6,759,395 B2 | 7/2004 | Rao et al. |
| 6,943,155 B2 | 9/2005 | Lichtenberger et al. |
| 7,303,762 B2 | 12/2007 | New |
| 7,651,995 B2 | 1/2010 | New |
| 8,314,058 B2 | 11/2012 | New |
| 8,329,208 B2 | 12/2012 | Harrison et al. |
| 8,580,296 B2 | 11/2013 | Harrison et al. |
| 8,865,203 B2 | 10/2014 | Harrison et al. |
| 8,975,238 B2 | 3/2015 | Guan et al. |
| 9,801,896 B2 | 10/2017 | Guan et al. |
| 9,925,208 B2 | 3/2018 | Guan et al. |
| 9,931,356 B2 | 4/2018 | Harrison et al. |
| 2002/0013905 A1 | 1/2002 | Hamada |
| 2002/0106345 A1 | 8/2002 | Uhrich et al. |
| 2002/0164369 A1 | 11/2002 | Rao et al. |
| 2004/0028729 A1 | 2/2004 | Shojaei |
| 2005/0142187 A1 | 6/2005 | Treacy et al. |
| 2005/0158382 A1 | 7/2005 | Cruz et al. |
| 2005/0171034 A1 | 8/2005 | Halevie-Goldman |
| 2005/0181047 A1 | 8/2005 | Romero |
| 2005/0191349 A1 | 9/2005 | Boehm et al. |
| 2005/0267023 A1 | 12/2005 | Sinclair et al. |
| 2006/0013905 A1 | 1/2006 | Tehoharides et al. |
| 2006/0069059 A1 | 3/2006 | Schaller et al. |
| 2006/0094782 A9 | 5/2006 | Wong et al. |
| 2006/0127506 A1 | 6/2006 | Hebert |
| 2006/0130160 A1 | 6/2006 | Dumas et al. |
| 2006/0280789 A1 | 12/2006 | Ueki et al. |
| 2007/0196272 A1 | 8/2007 | Eddington |
| 2007/0196501 A1 | 8/2007 | Paterson et al. |
| 2007/0265211 A1 | 11/2007 | Rath et al. |
| 2008/0206333 A1 | 8/2008 | Freedman |
| 2008/0234380 A1 | 9/2008 | Shapiro |
| 2008/0279931 A1 | 11/2008 | Morrow |
| 2009/0088404 A1 | 4/2009 | Freedman et al. |
| 2009/0110729 A1 | 4/2009 | Giovannone |
| 2009/0197824 A1 | 8/2009 | Freedman et al. |
| 2010/0056627 A1 | 3/2010 | Higuchi et al. |
| 2010/0222435 A1 | 9/2010 | Oberegger et al. |
| 2011/0027342 A1 | 2/2011 | MacDonald et al. |
| 2011/0027360 A1 | 2/2011 | Harrison et al. |
| 2011/0064712 A1 | 3/2011 | Amato |
| 2012/0177602 A1 | 7/2012 | New |
| 2013/0004563 A1 | 1/2013 | Shah et al. |
| 2013/0129792 A1 | 5/2013 | Harrison et al. |
| 2013/0142847 A1 | 6/2013 | MacDonald et al. |
| 2013/0149350 A1 | 6/2013 | Harrison et al. |
| 2014/0220129 A1 | 8/2014 | Guan et al. |
| 2014/0370108 A1 | 12/2014 | Harrison et al. |
| 2015/0087679 A1 | 3/2015 | Helmi et al. |
| 2015/0164935 A1 | 6/2015 | Guan et al. |
| 2015/0283161 A1 | 10/2015 | Guan et al. |
| 2015/0367366 A1 | 12/2015 | Edwards et al. |
| 2016/0361339 A1 | 12/2016 | Harrison et al. |
| 2017/0020815 A1 | 1/2017 | Gutierrez et al. |
| 2018/0000881 A1 | 1/2018 | Fritz |
| 2019/0022119 A1 | 1/2019 | Guan et al. |
| 2019/0038573 A1 | 2/2019 | Westphal et al. |
| 2019/0060345 A1 | 2/2019 | Harrison et al. |
| 2020/0129572 A1 | 4/2020 | Rogulja et al. |
| 2020/0246404 A1 | 8/2020 | Yucel et al. |

FOREIGN PATENT DOCUMENTS

| | | |
|---|---|---|
| CA | 2677053 | 8/2008 |
| CA | 2769682 | 2/2010 |
| CA | 2769490 | 2/2011 |
| CA | 2769582 | 2/2011 |
| CN | 101012336 | 8/2007 |
| CN | 101677543 | 3/2010 |
| CN | 102695514 | 9/2012 |
| CN | 105232515 | 1/2016 |
| CN | 105476982 | 4/2016 |
| CN | 106714810 | 5/2017 |
| CN | 108853085 | 11/2018 |
| CN | 111265509 | 6/2020 |
| DE | 19839443 | 3/2000 |
| DE | 102005024614 | 11/2006 |
| EP | 0136464 | 4/1985 |
| EP | 1731596 | 12/2006 |
| EP | 2149369 | 2/2010 |
| EP | 2193787 | 6/2010 |

(56) References Cited

FOREIGN PATENT DOCUMENTS

| | | | |
|---|---|---|---|
| EP | 2464358 A | 6/2012 | |
| EP | 2512490 | 10/2012 | |
| EP | 2949331 | 12/2015 | |
| JP | S60-72815 | 4/1985 | |
| JP | H01193206 | 8/1989 | |
| JP | H05271067 | 10/1993 | |
| JP | 2001-514234 | 9/2001 | |
| JP | 2002504514 | 2/2002 | |
| JP | 2002538173 | 11/2002 | |
| JP | 2003155242 | 5/2003 | |
| JP | 2005320354 | 11/2005 | |
| JP | 2007508248 | 4/2007 | |
| JP | 2008163009 | 7/2008 | |
| JP | 2010-518021 | 5/2010 | |
| JP | 2015214518 A | 12/2015 | |
| JP | 5877935 | 3/2016 | |
| JP | 2016074725 | 5/2016 | |
| RU | 2014837 | 6/1994 | |
| RU | 2018314 | 8/1994 | |
| RU | 2246939 | 2/2005 | |
| WO | WO-99/11290 | 3/1999 | |
| WO | WO-99/43336 | 9/1999 | |
| WO | WO-00/51643 | 9/2000 | |
| WO | WO-01/12155 | 2/2001 | |
| WO | WO-02/49637 | 6/2002 | |
| WO | WO-02/083136 | 10/2002 | |
| WO | WO-02/092112 | 11/2002 | |
| WO | WO-2005/034920 | 4/2005 | |
| WO | WO-2006/044202 | 4/2006 | |
| WO | WO-2006/079212 | 8/2006 | |
| WO | WO-2006/125483 | 11/2006 | |
| WO | WO-2007/095092 | 8/2007 | |
| WO | WO-2007/133981 | 11/2007 | |
| WO | WO-2008/006581 | 1/2008 | |
| WO | WO-2008/065502 | 6/2008 | |
| WO | WO-2008/095142 | 8/2008 | |
| WO | WO-2010/008619 | 1/2010 | |
| WO | WO-2010/009449 | 1/2010 | |
| WO | WO-2010/027014 | 3/2010 | |
| WO | WO-2010/063756 | 6/2010 | |
| WO | WO-2011/012989 | 2/2011 | |
| WO | WO-2011/012990 | 2/2011 | |
| WO | WO-2012/012902 | 2/2012 | |
| WO | WO-2014/059522 | 4/2014 | |
| WO | WO-2015/159155 | 10/2015 | |
| WO | WO-2016/204657 | 12/2016 | |
| WO | 2024/238657 A2 | 11/2024 | |

OTHER PUBLICATIONS

U.S. Appl. No. 12/024,059 non-final Office Action mailed Oct. 3, 2011, Non-patent literature.
U.S. Appl. No. 12/182,036 Final Office Action mailed Dec. 30, 2013.
U.S. Appl. No. 12/182,036 Office Action dated Feb. 23, 2012.
U.S. Appl. No. 12/182,036 Office Action dated Mar. 15, 2013.
U.S. Appl. No. 12/845,555 Final Office Action mailed Aug. 29, 2012.
U.S. Appl. No. 12/845,555 Non-Final Office Action dated Nov. 8, 2011.
U.S. Appl. No. 12/845,555 Non-Final Office Action dated Oct. 8, 2013.
U.S. Appl. No. 12/845,555 Office Action dated Jun. 5, 2014.
U.S. Appl. No. 12/845,600 Final Office Action mailed Aug. 21, 2012.
U.S. Appl. No. 12/845,600 Office Action mailed Nov. 8, 2011.
U.S. Appl. No. 13/706,188 Office Action dated Jun. 5, 2014.
U.S. Appl. No. 13/706,188 Office Action dated Oct. 9, 2013.
U.S. Appl. No. 13/714,246 Non-Final Office Action mailed Apr. 24, 2013.
U.S. Appl. No. 13/811,772 Office Action dated Aug. 9, 2016.
U.S. Appl. No. 13/811,772 Office Action dated Dec. 12, 2016.
U.S. Appl. No. 13/811,772 Office Action dated Jan. 14, 2016.
U.S. Appl. No. 13/811,772 Office Action dated Jan. 29, 2014.
U.S. Appl. No. 13/811,772 Office Action mailed Aug. 13, 2015.
U.S. Appl. No. 13/811,772 Office Action mailed Nov. 19, 2014.
U.S. Appl. No. 14/247,061 Office Action dated May 22, 2014.
U.S. Appl. No. 14/247,061 Office Action dated Oct. 30, 2014.
U.S. Appl. No. 14/436,418 Office Action dated Mar. 22, 2016.
U.S. Appl. No. 14/436,418 Office Action dated Mar. 22, 2017.
U.S. Appl. No. 14/436,418 Office Action dated Nov. 23, 2016.
U.S. Appl. No. 14/472,204 Office Action dated Feb. 23, 2016.
U.S. Appl. No. 14/628,623 Office Action dated Aug. 25, 2016.
U.S. Appl. No. 14/628,623 Office Action dated Jan. 20, 2016.
U.S. Appl. No. 14/628,623 Office Action dated Jun. 2, 2017.
U.S. Appl. No. 15/245,105 Office Action dated Apr. 4, 2017.
U.S. Appl. No. 15/902,877 Non-Final Office Action dated Feb. 5, 2019.
U.S. Appl. No. 15/932,359 Office Action dated Jun. 26, 2019, Non-patent literature.
"New S-Adenosilmethionine Salts and the Process for their Preparation," Research Disclosure, Mason Publication, Hampshire, GB, 1991; 332: pp. 927-933.
Alexander, "Hypertension and the pathogenesis of atheroscierosis oxidative stress and the mediation of arterial inflammatory response: A new perspective," Hypertension, 1995; 25: pp. 155-161.
Anstee et al., "S-adenosylmethionine (SAMe) therapy in liver disease: A review of current evidence and clinical utility," Journal of Hepatology, 2012; 57: pp. 1097-1109.
Australia Patent Application No. 2013332209 Patent Examination Report No. 1 dated Nov. 24, 2015.
Authors Unknown, "Final report on the amended safety assessment of Propyl Gallate," International Journal of Toxicology, 2007; 26(3): pp. 89-118.
Baldrick, "Pharmaceutical Excipient Development: The Need for Preclinical Guidance," Regul Toxicol Pharmacol, 2000; 32(2): pp. 210-218.
Bottiglieri et al., "Ademetionine (S-adenosylomethionine) neuropharmacology: implications for drug therapies in psychiatric and neurological disorders," Exp Opin Invest Drugs, 1997; 6(4): pp. 417-426.
Bottiglieri et al., "Folate, vitamin B12, and S-adenosylmethionine," Psychiatr Clin North Am, 2013; 36(1): pp. 1-13.
Bottiglieri et al., "Transmethylation in depression," Alabama J Med Sci, 1988; 25(3): pp. 296-301.
Bourdet et al., "Saturable absorptive transport of the hydrophilic organic cation ranitidine in caco-2 cells: Role of pH-dependent organic cation uptake system and P-glycoprotein," Pharm. Res., 2006; 23(6): pp. 1165-1177.
Brown et al., "Novel Protective Mechanisms for S-Adenosyl-L-methionine against Acetaminophen Hepatotoxicity: Improvement of Key Antioxidant Enzymatic Function," Toxicol Lett, 2012; 212(3): pp. 320-328.
Canadian Patent Application No. 2888302 Examiners Report dated Sep. 11, 2015.
Canadian Patent Application No. 2888302 Office Action dated May 13, 2015.
Canadian Patent Application No. CA 2888302 Examiners Report dated Jan. 4, 2016.
Caro et al., "Inhibition of CYP2E1 catalytic activity in vitro by S-adenosyl-L-methionine," Biochemical Pharmacology, 2005; 69: pp. 1081-1093.
Cavallaro et al., "S-adenosylmethionine prevents oxidative stress and modulates glutathione metabolism in TgCRND8 mice fed a B-vitamin deficient diet," J Alzheimers Dis., 2010; 20(4): pp. 997-1002.
Chen et al., "Treatment of Lesch-Nyhan disease with S-adenosylmethionine: experience with five young Malaysians, including a girl," Brain Dev., 2014; 36(7): pp. 593-60.
Chinese Patent Application No. 201380054342.5 First Office Action dated Feb. 26, 2016.
Chinese Patent Application No. 201610230503.7 First Office Action dated Mar. 8, 2018.
Cimino et al., "Age-related modification of dopaminergic and β-adrenergic receptor system: Restoration to normal activity by

(56) References Cited

OTHER PUBLICATIONS modifying membrane fluidity with s-adenosylmethionine," Life Sciences, 1984; 34(21): pp. 2029-2039.
Deli, "Potential use of tight junction modulators to reversibly open membranous; barriers and improve drug delivery," Biochim Biophys Acta, 2009; 788(4): pp. 892-910.
Di Padova, "S-Adenosylmethionine in the treatment of osteoarthritis," The American Journal of Medicine, 1987; 83(5A): pp. 60-65.
Dirocco et al., "Brief Report: S-Adenosyl-Methionine improves depression in patients with Parkinson's disease in an open-label clinical trial," Mov Disorders, 2000; 15(6): pp. 1225-1229.
Dubey et al., "Potentiation of arsenic neurotoxicity by folate deprivation: protective role of S-adenosyl methionine," Nutr Neurosci, 2007; 10(5-6): pp. 199-204.
Duizer et al. "Absorption enhancement, structural changes in tight junctions and cytotoxicity caused by palmitoyl carnitine in Caco-2 and IEC-18 cells," J Pharmacol Exp Ther., 1998; 287(1): pp. 395-402.
EP 08728778.5 Extended Search Report issued Dec. 7, 2012.
EP 10803973.6 Search Report and Search Opinion issued Nov. 23, 2012.
EP 13834351.2 European Search Report dated Jul. 31, 2014.
EP 15162054.9 Application Communication dated Jul. 14, 2017.
EP 15162054.9 Extended Search Report issued Oct. 7, 2015.
EP10751713.8 Search Report dated Jan. 25, 2013.
Eudragit L 100, [online] [retrieved on Aug. 25, 2012] <URL: http://eudragit.evonik.com/product/eudragit/en/products-services/eudragit-products/enteric-formulations/l-100/Pages/default.aspx>.
Eudragit S 100, [online] [retrieved on Aug. 25, 2012] <URL: http://eudragit.evonik.com/product/eudragit/en/products-services/eudragit-products/enteric-formulations/s100/Pages/default.aspx>.
Feng et al., "Correlation of antimutagenic activity and suppression of CYP1A with the lipophilicity of alkyl gallates and other phenolic compounds," Mutation Research, 2003; 537(1): pp. 101-108.
Friedel, "S-Adenosyl-L-methionine—A review of its pharmacological properties and therapeutic potential in liver dysfunction and affective disorders in relation to its physiological role in cell metabolism," Drugs, 1989; 38(3): pp. 389-416.
Furujo et al., "S-adenosylmethionine treatment in methionine adenosyltransferase deficiency, a case report," Mol Genet Metab., 2012; 105(3): pp. 516-518.
Gentile et al., "Age-associated decline of hepatic handling of cholephilic anions in humans is reverted by S-adenosylmethionine (SAMe)," Scan. J.Clin Lab Investigation, 1990; 50(5): pp. 565-571.
Giulidori et al., "Pharmacokinetics of S-adenosyl-L-methionine in healthy volunteers", Eur. J. Clin. Pharmacol., 1984; 27: pp. 119-121.
Gren et al., "Porous cellulose matrices containing lipophilic release modifiers—a potential oral extended-release system," Intl. J. Pharmaceutics, 1999; 184: pp. 7-19.
Hirshberg Foundation for Pancreatic Cancer Research, About the Foundation; Pancreatic Cancer; Research; Patients & Caregivers. 5 pages, downloaded on Aug. 19, 2016 from: http://pancreatic.org/pancreatic-cancer/about-the-pancreas/prognosis.
Hochman et al., "Mechanisms of absorption enhancement and tight junction regulation," Journal of Controlled Release, 1994; 29(3): pp. 253-267.
Holquist and Fava. "FDA safety page: Delayed-release vs. extended-release Rxs." Drug Topics Aug. 14, 2012 [retrieved online] http://license.icopyright.net/user/viewFreeUse.act?fuid=MTY1MDlyNjY%3D [online], 2 pages.
India Patent Application No. 4151/DELNP/2015 Examination Report dated Mar. 20, 2018.
Israel Patent Application No. 243585 Examination Report dated Jul. 26, 2017.
Israel Patent Application No. 243585 Office Action dated Jun. 15, 2016.
Jacobsen, et al., "Oral S-adenosylmethionine in primary fibromyalgia. Double-blind clinical evaluation," Scand J Rheumatol, 1991; 20(4): pp. 294-302.

Japan Patent Application No. 2015-238622 Office Action (and summary in English) dated Jun. 20, 2017.
Japanese Patent Application No. 2015-537091 Official Action dated Sep. 29, 2015 with English translation.
Japanese Pharmaceutical Excipients Directory, First Edition, Jan. 14, 1994, pp. 148, 137 and 16.
Kaye et al., "Metabolism of Exogenous S-Adenosyl-L-Methionine in Patients with Liver Disease," Drugs, 1990; 40: pp. 124-128.
Korean Patent Application No. 10-2015-7012788 Notice of Final Rejection dated Apr. 27, 2016.
Korean Patent Application No. 10-2015-7012788 Office Action dated Dec. 7, 2015.
Korean Patent Application No. 10-2015-7012788 Office Action dated Jan. 2, 2017 (English translation not provided).
Krzystanek et al., "S-adenozylo L-metionina w schorzeniach OUN. S-adenosyl L-methionine in CNS diseases," Psychiatria Polska, 2011; 45(6): pp. 923-931. (English abstract provided).
Labiche et al., "Clinical trials for Cytoprotection in stroke," NeuroRx: The Journal of the American Society for Experimental Neuro Therapeutics, 2004; 1(1): pp. 46-70.
Laudanno et al., "La prostaglandina E 1 (misoprostol) y el SAMe en la prevencion de las gastritis hemorragicas inducida por aspirins, en el hombre. Estudio endoscopico, histologico e histoquimico," Acta Gastroenterol Lationamerica, 1984; 14(4): pp. 289-293. (English abstract provided).
Laudanno, "Cytoprotective effect of S-Adenosylmethionine compared with that of misoprostol against ethanol-, aspirin-, and stress-induced gastric damage," The American Journal of Medicine, 1987; 83(Supp 5A): pp. 43-47.
Lee et al., "Hypothesis: a unifying mechanism for nutrition and chemicals as lifelong modulators of DNA hypomethylation," Environ Health Perspect, 2009; 117: pp. 1799-1802.
Li et al., "Effects of S-adenosylmethionine and methylthioadenosine on inflammation-induced colon cancer in mice," Carcinogenesis, 2012; 33(2): pp. 427-435.
Linnebank et al., "s-Adenosylmethionine is decreased in the cerebrospinal fluid of patients with Alzheimer's disease," Neurodegenerative Disease, 2010; 7: pp. 373-378.
Loenen, S-Adenosylmethionine: jack of all trades and master of everything? Biomedical Society Transactions, 2006; 34(2): pp. 330-333.
Lu and Mato, "S-Adenosylmethionine in cell growth, apoptosis and liver cancer," Journal of Gastroenterology and Hepatology, 2008; 23 Supp:S73-77.
Lu and Mato, "S-adenosylmethionine in liver health, injury, and cancer," Physiol Rev, 2012; 92(4): pp. 1515-1542.
Lu, Shelly, "S-Adenosylmethionine," The International Journal of Biochemistry & Cell Biology, 2000; 32: pp. 391-395.
Luo et al., "S-adenosylmethionine inhibits the growth of cancer cells by reversing the hypomethylation status of c-myc and H-ras in human gasatric cancer and colon cancer," Int. J. of Biological Sciences, 2010; 6(7): pp. 784-795.
Manna et al., "Age-related decline in S-adenosylmethionine and protein methyl esterification levels in bovine lenses," Arch Gerontol Geriatr, 1992; Supp. 3: pp. 237-248.
Material Safety Data Sheet of S-Adenosyl-L-methionine disulfate tosylate, United States Pharmacopeia [online], Dec. 27, 2011 http://www.usp.org/pdf/EN/referenceStandards/msds/1012134.pdf, [retrieved online Aug. 16, 2012], 4 pages.
Mato et al., "S-adenosylmethionine in alcoholic liver cirrhosis: a randomized, placebo-controlled, double-blind, multicenter clinical trial," Journal of Hepatology, 1999; 30(6): pp. 1081-1089.
Mato et al., "S-Adenosylmethionine synthesis: Molecular mechanisms and clinical implications," Pharmacol. Ther., 1997; 73(3): pp. 265-280.
McMillan et al., "S-adenosyl-L-methionine: transcellular transport and uptake by Caco-2 cells and hepatocytes," Journal of Pharmacy and Pharmacology, 2005; 57: pp. 599-605.
Najm et al., "S-Adenosyl methionine (SAMe) versus celecoxib for the treatment of osteoarthritis symptoms: A double-blind cross-over trial," [ISRCTN36233495] BMC Musculoskeletal Disorders, 2004; 5: 15 pages.

(56) References Cited

OTHER PUBLICATIONS

New Review Article of Pharmaceutics, Apr. 10, 1987, Third Edition, pp. 262-268.
Papakostas et al., "Folates and S-adenosylmethionine for major depressive disorder," Can J Psychiatry, 2012; 57(7): pp. 406-413.
Pascale et al., "Chemoprevention of hepatocarcinogenesis:S-adenosyl-L-methionine," Alcohol, 2002; 27: pp. 193-198.
PCT/CA2011/050462 International Preliminary Report on Patentability, issued Jan. 29, 2013.
PCT/CA2011/050462 Third Party Observation retrieval date Oct. 29, 2012.
PCT/CA2013/000876 International Preliminary Report on Patentability dated Apr. 21, 2015.
PCT/CA2013/000876 International Search Report and Written Opinion dated Dec. 5, 2013, 13 pages.
PCT/IB2010/001877 International Preliminary Report on Patentability, issued Jan. 31, 2012.
PCT/IB2010/001879 International Preliminary Report on Patentability, issued Jan. 31, 2012.
PCT/US09/51076 Written Opinion dated Feb. 17, 2010.
PCT/US2008/052726 International Preliminary Report on Patentability, issued Dec. 30, 2008.
PCT/US2009/036703 International Preliminary Report on Patentability, mailed Jan. 18, 2011.
PCT/US2009/051076 International Preliminary Report on Patentability, mailed Jan. 27, 2011.
Poirier et al., "Blood S-adenosylmethionine concentrations and lymphocyte methylenetetrahydrofolate reductase activity in diabetes mellitus and diabetic nephropathy," Metabolism, 2001; 50(9): pp. 1014-1018.
Price et al., "Effect of butylated hydroxytoluene, curcumin, propyl gallate and thiabendazole on cytochrome P450 forms in cultured human hepatocytes," Xenobiotica, 2008; 38(6): pp. 574-586.
Proctor et al., "Mechanisms underlying saturable intestinal absorption of metformin," Drug Metab. Dispos., 2008; 36(8): pp. 1650-1658.
Remington et al., "A Phase II randomized clinical trial of a nutritional formulation for cognition and mood in Alzheimer's disease," Journal of Alzheimer's Disease, 2015; 45: pp. 395-405.
Russian Patent Application No. 2015118235 Office Action issued Sep. 14, 2015.
Sahelian, "SAM-e" Datasheet [online][retrieved on Aug. 15, 2011 from internet archive dated Jul. 3, 2004], <original URL:http://www.raysahelian.com/sam-e.html> <internet archive URL:http://web.archive.org/web/20040703065710/http://www.raysahelian.com/sam-e.html>.
Sahin et al., "Inhibition of angiogenesis by S-adenosylmethionine," Biochemical and Biophysical Research Communication, 2011; 408: pp. 145-148.
Shea et al., "S-adenosyl methionine: a natural therapeutic agent effective against multiple hallmarks and risk factors associated with Alzheimer's disease," Alzheimers Disease, 2008; 13(1): pp. 67-70.
Shinitzky et al., "Dynamics of the hydrocarbon layer in liposomes of lecithin and sphingomyelin containing dicetylphosphate," J. Biol. Chem., 1974; 249(8): pp. 2652-2657.
Singapore Patent Application No. 11201503048T Supplementary Examination Report dated Nov. 6, 2015.
Soeken et al., "Safety and efficacy of S-adenosylmethionine (SAMe) for osteoarthritis," J Fam Pract, 2002; 51(5): pp. 425-443.
Stewart, "Comparison of Intestinal Permeabilities Determined in Multiple in Vitro and in Situ Models: Relationship to Absorption in Humans," Pharmaceutical Research, 1995; 12(5): pp. 693-699.
Stramentinoli et al., "Intestinal absorption of S-Adenosyl-L-Methionine," The Journal of Pharmacology and Experimental Therapeutics, 1979; 209(3): pp. 323-326.
Stramentinoli et al., "Pharmacologic aspects of S-adenosylmethionine-Pharmacokinetics and pharmacodynamics," Am J Med, 1987; 83(5): pp. 35-42.
Stramentinoli, "Adomet as a Drug Pharmacokinetic and Pharmacological Aspects," Biol Methylation and Drug Design, R.T. Borchardt, New Jersey, Humana Press, 1986: pp. 315-326.
Suchy et al., "Dietary supplementation with S-adenosylmethionine delays the onset of motor neuron pathology in a murine model of amyotrophic lateral sclerosis," Neuromolecular Med., 2010; 12(1): pp. 86-97.
Szyf, "Epigenetic therapeutics in autoimmune disease," Clin Rev Allergy Immunol, 2010; 39(1): pp. 62-77.
Whitehead et al., "Safe and Effective Permeation Enhancers for Oral Drug Delivery," Pharm. Res., 2008; 25(8): pp. 1783-1788.
Williams et al., "S-adenosylmethionine (SAMe) as treatment for depression: a systematic review," Clin Invest Med, 2005; 28(3): pp. 132-139.
Wu et al., "Synthesis of gallic acid esters and their antibloodplatelet aggregation," Fine Chemical, 1998; 15(4): pp. 9-12.
www.merriam-webster.com/dictionary/food retrieved on Nov. 4, 2011.
Yang et al., "Lupus autoimmunity altered by cellular methylation metabolism," Autoimmunity, 2013; 46(1): pp. 21-31.
Yang et al., "Pharmacokinetic properties of S-denosylmethionine after oral and intravenous administration of its tosylate disulfate salt: A multiple-dose, open-;label, parallel-group study in healthy Chinese volunteers," Clin. Therapeutics, 2009; 31(2): pp. 311-320.
Ying et al., "Determination and pharmacokinetics of S-adenosylmethionine in human plasma by solid phase extraction-LC/MS," J China Pharmaceutical University, 2009; 40(1): pp. 67-71 (with English translation).
Yuhua et al., "Study on the synthesis and application of cottonseed fatty acid diethanolamide," Fine Chemicals, 1998; 15: pp. 9-12.
Zhao et al., "Inhibitory effect of S-adenosylmethionine on the growth of human gastric cancer cells in vivo and in vitro," Chin J Cancer, 2010; 29(8): pp. 752-760.
Zhang et al., "Association of magnesium intake with sleep duration and sleep quality: Findings from the Cardia Study," Sleep, 2021; 45(4): pp. 1-8.
Abbasi et al., "The effect of magnesium supplementation on primary insomnia in elderly: A double-blind placebo-controlled clinical trial," J Res Med Sci, 2012; 17: pp. 1161-1169.
Algeri et al., "Changes in rat brain noradrenaline and serotonin metabolism after administration of S-Adenosylmethionine," Biochemical and Pharmacological Roles of Adenosylmethionine and the Central Nervous System, 1979; pp. 81-87.
Ashton, "Guidelines for the rational use of benzodiazepines. When and what to use," Drugs, 1994; 48(1): pp. 25-40.
Berryhill et al., "Effect of wearables on sleep in healthy individuals: a randomized crossover trial and validation study," J Clin Neurol, 2020; 16(5): pp. 775-783.
Billyard et al., "Dietary magnesium deficiency decreases plasma melatonin in rats," Magnesium Research, 2006; 19(3): pp. 157-161.
Bottiglieri et al., "S-adenosylmethionine influences monoamine metabolism," The Lancet, 1984; 324(8396): p. 224.
Bottiglieri, "S-adenosyl-L-methionine (SAMe): From the bench to the bedside-molecular basis of a pleiotrophic molecule," Am J Clin Nutr, 2002; 76(5): pp. 1151S-1157S.
Bottiglieri, "Folate, vitamin B12, and S-adenosylmethionine," The Psychiatric clinics of North America, 2013; 36(1): pp. 1-13.
Brandt et al., "Benzodiazepines and Z-Drugs: An Updated Review of Major Adverse Outcomes Reported on in Epidemiologic Research," Drugs in R&D, 2017; 17(4): pp. 493-507.
Byun et al., "Safety and Efficacy of Gamma-Aminobutyric Acid from Fermented Rice Germ in Patients with Insomnia Symptoms: A Randomized, Double-Blind Trial," J Clin Neurol, 2018; 14(3): pp. 291-295.
Caro et al., "Antioxidant properties of S-adenosyl-L-methionine in $Fe^{2+}$-initiated oxidations'" Free Radic. Biol. Med., 2004; 36(10): pp. 1303-1316.
Deckert et al., "Adenosinergic psychopharmaceuticals: just an extra cup of coffee?" J of Psychopharmacology, 1990: 183-187.
Deckert et al., "Adenosinergic psychopharmaceuticals?" Trends Pharmacol Sci, 1989;10: pp. 99-100.

(56) References Cited

OTHER PUBLICATIONS

Delgado et al., "Validation of digital visual analog scale pain scoring with a traditional paper-based visual analog scale in adults," JAAOS: Global Research and Reviews, 2018; 2(3).

Dolan-Sewell et al., "NIH State-of-the-Science Conference on Chronic Insomnia," Journal of Clinical Sleep Medicine, 2005; 1(4): pp. 335-336.

Edinoff et al., "Benzodiazepines: Uses, Dangers, and Clinical Considerations," Neurology international, 2021; 13(4), 594-607.

El Khoudary et al., "The menopause transition and women's health at midlife: a progress report from the Study of Women's Health Across the Nation (SWAN)," Menopause, 2019; 26(10), 1213-1227.

Erland et al., "Melatonin Natural Health Products and Supplements: Presence of Serotonin and Significant Variability of Melatonin Content," J Clin Sleep Med, 2017; 13(2): pp. 275-281.

Fatemeh et al., "Effect of melatonin supplementation on sleep quality: a systematic review and meta-analysis of randomized controlled trials," Journal of neurology, 2022; 269(1): pp. 205-216.

Filaci et al., "S-adenosil-L-methionine is able to reverse the immunosuppressive effects of chenodeoxycholic acid in vitro", Int J Immunopharmacol. 1997; 19: pp. 157-165.

Gröber et al., "Magnesium in prevention and therapy," Nutrients, 2015; 7(9): pp. 8199-8226.

Gualano et al., "Anti-inflammatory activity of S-adenosyl-L-methionine: Interference with the eicosanoid system", Pharmacol. Res. Commun., 1983; 15(7): pp. 683-696.

Gunja, "The clinical and forensic toxicology of Z-drugs," J Med Toxicol., 2013; 9 (2): pp. 155-162.

Hartzler, "Which Type of Magnesium is Best?" Pharm To Table, [online], Oct. 19, 2020, [retrieved on Aug. 12, 2024]. Retrieved from the Internet: <URL: https://pharmtotable.life/2020/09/19/which-type-of-magnesium-is-best/>.

Hidese et al., "Effects of L-Theanine Administration on Stress-Related Symptoms and Cognitive Functions in Healthy Adults: A Randomized Controlled Trial," Nutrients, 2019; 11(10): 2362.

Hilditch JR et al., "A menopause-specific quality of life questionnaire: development and psychometric properties," Maturitas, 1996; 24(3): pp. 161-175.

Jo et al., "Polygonatum sibiricum rhizome promotes sleep by regulating non-rapid eye movement and GABAergic/serotonergic receptors in rodent models," Biomed Pharmacother, 2018; 105: pp. 167-175.

Kadakia et al., "Phase II evaluation of S-adenosyl-L-methionine (SAMe) for the treatment of hot flashes," Supportive Care Cancer, 2016; 24(3): pp. 1061-1069.

Kaida et al., "Validation of the Karolinska sleepiness scale against performance and EEG variables," Clinical Neurophysiology, 2006; 117(7): pp. 1574-1581.

Kim et al., "GABA and L-theanine mixture decreases sleep latency and improves NREM sleep," Pharm Biol, 2019; 57 (1): pp. 64-72.

Kravitz et al., "Sleep difficulty in women at midlife: a community survey of sleep and the menopausal transition," Menopause, 2003; 10(1): 19-28.

Lyon et al., "The effects of L-theanine (Suntheanine®) on objective sleep quality in boys with attention deficit hyperactivity disorder (ADHD): a randomized, double-blind, placebo-controlled clinical trial," Altern Med Rev., 2011; 16 (4): pp. 348-354.

Mayo Foundation for Medical Education and Research, "Magnesium supplement (oral route) side effects," Mayo Clinic, [online], [retrieved Wayback Machine capture of Nov. 9, 2015]. Retrieved from the Internet: <URL: https://web.archive.org/web/20151109113135/http://www.mayoclinic.org:80/drugs-supplements/magnesium-supplement-oral-route-parenteral-route/side-effects/drg-20070730?p=1>.

Ngo et al., "An Updated Review on Pharmaceutical Properties of Gamma-Aminobutyric Acid," Molecules (Basel, Switzerland), 2019; 24(15).

NIH State-of-the-Science Conference Statement on manifestations and management of chronic insomnia in adults. NIH Consens State Sci Statements. Jun. 13-15, 2005;22(2):1-30. PMID: 17308547.

Nobre et al., "L-theanine, a natural constituent in tea, and its effect on mental state," Asia Pac J Clin Nutr, 2008; 17(1): pp. 167-168.

Oketch-Rabah et al., "United States Pharmacopeia (USP) Safety Review of Gamma-Aminobutyric Acid (GABA)," Nutrients, 2021; 13(8).

Paterson et al, "A translational, caffeine induced model of onset insomnia in rats and healthy volunteers," Psychopharmacology (Berl), 2007; 191: pp. 943-950.

Petroff, "GABA and glutamate in the human brain," The Neuroscientist, 2002; 8(6): pp. 562-573.

Ryba et al., "Z-drugs and Falls: A Focused Review of the Literature," Sr Care Pharm, 2020; 35(12): pp. 549-554.

Sarris et al., "L-theanine in the adjunctive treatment of generalized anxiety disorder: A double-blind, randomised, placebo-controlled trial," Journal of psychiatric research, 2019; 110, 31-37.

Shaver et al., "Sleep and menopause: a narrative review," Menopause, 2015; 22(8), 899-915.

Shinomiya et al., "Effects of chlorogenic acid and its metabolites on the sleep-wakefulness cycle in rats," Eur J Pharmacol, 2004; 504: pp. 185-189.

U.S. Department of Health and Human Services, Office of Dietary Supplements, "Magnesium, Fact Sheet for Health Professionals," NIH Office of Dietary Supplements, [online], updated Jun. 2022, [retrieved on May 15, 2024]. Retrieved from the Internet: <URL: https://ods.od.nih.gov/factsheets/Magnesium-HealthProfessional/>.

Watanabe et al., "GABA and GABA receptors in the central nervous system and other organs," International Review of Cytology, 2002; 213: pp. 1-47.

Yokogoshi et al., "Effect of theanine, r-glutamylethylamide, on brain monoamines and striatal dopamine release in conscious rats," Neurochem Res, 1998; 23(5): pp. 667-673.

Yu et al., "Development of short forms from the PROMIS™ sleep disturbance and sleep-related impairment Item Banks," Behavioral Sleep Medicine, 2012; 10(1): pp. 6-24.

Dugovic, "Role of serotonin in sleep mechanisms," Revue neurologique, 2001; 157(11 Pt 2): pp. S16-S19. Abstract only provided.

Kajimoto et al., "Hypotensive effect of fermented milk containing gamma-aminobutyric acid (GABA) in subjects with high normal blood pressure," Journal of the Japanese Society for Food Science and Technology (Japan), 2004; 51(2): pp. 79-86. (English abstract included).

Matusbara et al., "Effects of GABA supplementation on blood pressure and safety in adults with mild hypertension," Japanese Pharmacology and Therapeutics, 2002; 30(11): pp. 963-972. Abstract only provided.

PCT/US2024/029467 International Search Report and Written Opinion mailed Nov. 20, 2024.

COMPOSITIONS COMPRISING S-ADENOSYLMETHIONINE AND A GALLIC ACID ESTER

CROSS REFERENCE TO RELATED APPLICATIONS

This application is a continuation of U.S. patent application Ser. No. 16/727,610, filed Dec. 26, 2019, which is a continuation of U.S. patent application Ser. No. 15/932,359, filed Feb. 16, 2018, now Abandoned, which is a continuation of U.S. patent application Ser. No. 14/628,623, filed Feb. 23, 2015, now U.S. Pat. No. 9,925,208, issued Mar. 27, 20218, which is a continuation of U.S. patent application Ser. No. 14/247,061, filed Apr. 7, 2014, now U.S. Pat. No. 8,975,238, issued Mar. 10, 2015, which is a continuation of International Patent Application No. PCT/CA2013/000876, filed Oct. 16, 2013, which claims the benefit of U.S. Provisional Application No. 61/715,138, filed Oct. 17, 2012, both of which are incorporated herein by reference in their entireties.

BACKGROUND OF THE INVENTION

S-adenosyl-L-methionine ("SAM-e" or "SAMe") is a naturally occurring compound that is present in almost every tissue throughout the body. Aside from water, SAMe is considered the second most common metabolic molecule-adenosine triphosphate (ATP) being the most common. SAMe is available as an over-the-counter dietary supplement in a number of countries and by prescription in Europe. Supplementation with exogenous SAMe has been tested and showed efficacious for the treatment of various ailments, including arthritis, Alzheimer's, liver disease and depression. Unfortunately, however, the uptake of exogenous SAMe is very low (<5%) and therefore large doses are required daily. Thus, there is a need for enhancing the delivery and thus efficacy of exogenous SAMe.

SUMMARY OF THE INVENTION

Provided herein are compositions, formulations, medicaments, uses, and methods for enhancing the delivery of exogenous S-Adenosyl-L-Methionine ("SAMe"). Also provided herein are compositions, formulations, medicaments, uses, and methods for increasing SAMe plasma levels. In certain embodiments, compositions, formulations, medicaments, uses, and methods described herein provide improved SAMe levels in vivo as compared to conventional dosage forms of SAMe.

In certain embodiments, provided herein are compositions, formulations, or medicaments comprising exogenous SAMe and one or more gallic acid ester. In some embodiments, a gallic acid ester provided herein is selected from the group consisting of methyl gallate, ethyl gallate, propyl gallate, butyl gallate, isobutyl gallate, isoamyl gallate, octyl gallate, dodecyl gallate, lauryl gallate, hexadecyl gallate, cetyl gallate, gallocatechol, gallocatechin, and epigallocatechin. In some embodiments, a gallic acid ester provided herein is ethyl gallate, isoamyl gallate, propyl gallate or octyl gallate.

In some embodiments, a gallic acid ester provided herein is ethyl gallate.

In some embodiments, a gallic acid ester provided herein is isoamyl gallate.

In some embodiments, a gallic acid ester provided herein is octyl gallate.

In a preferred embodiment, a gallic acid ester provided herein is propyl gallate.

In certain embodiments, compositions, formulations, medicaments, uses, and methods described herein provide improved SAMe levels in vivo as compared to conventional dosage forms of SAMe which lack gallic acid esters.

In some embodiments, provided herein are compositions, formulations, or medicaments comprising exogenous SAMe and one or more gallic acid esters, wherein the ratio (weight:weight) of said gallic acid ester to S-adenosylmethionine is from 5:1 to 1:400. In some embodiments, the ratio (weight:weight) of said gallic acid ester to S-adenosylmethionine is from 5:1 to 1:400. In some embodiments, the ratio (weight:weight) of said gallic acid ester to S-adenosylmethionine is from 5:1 to 1:100. In some embodiments, the ratio (weight:weight) of said gallic acid ester to S-adenosylmethionine is from 1:1 to 1:100. In some embodiments, the ratio (weight:weight) of said gallic acid ester to S-adenosylmethionine is from 1:2 to 1:80. In some embodiments, the ratio (weight:weight) of said gallic acid ester to S-adenosylmethionine is from 1:4 to 1:64. In some embodiments, the ratio (weight:weight) of said gallic acid ester to S-adenosylmethionine is from 4:1 to 1:80. In some embodiments, the ratio (weight:weight) of said gallic acid ester to S-adenosylmethionine is from 3:1 to 1:60. In some embodiments, the ratio (weight:weight) of said gallic acid ester to S-adenosylmethionine is from 2:1 to 1:40. In some embodiments, the ratio (weight:weight) of said gallic acid ester to S-adenosylmethionine is from 1:1 to 1:16. In some embodiments, the inventors have surprisingly discovered that ratios of gallic acid ester to SAMe may be optimized for different gallic acid esters. In some embodiments, provided herein are compositions comprising exogenous SAMe and ethyl gallate, isoamyl gallate or octyl gallate, wherein the weight ratio of ethyl gallate, isoamyl gallate or octyl gallate to SAMe is from 1:1 to 1:16. In some embodiments, provided herein are compositions comprising exogenous SAMe and ethyl gallate, wherein the weight ratio of ethyl gallate:SAMe is from about 1:1 to 1:100. In some embodiments, provided herein are compositions comprising exogenous SAMe and isoamyl gallate, wherein the weight ratio of isoamyl gallate:SAMe is from about 1:1 to 1:100. In some embodiments, provided herein are compositions comprising exogenous SAMe and octyl gallate, wherein the weight ratio of octyl gallate:SAMe is from about 1:1 to 1:100. In some embodiments, provided herein are compositions comprising exogenous SAMe and propyl gallate, wherein the weight ratio of propyl gallate:SAMe is from about 1:1 to 1:100. In some embodiments, provided herein are compositions comprising exogenous SAMe and propyl gallate, wherein the weight ratio of propyl gallate:SAMe is from about 1:2 to 1:80. In some embodiments, provided herein are compositions comprising exogenous SAMe and propyl gallate, wherein the weight ratio of propyl gallate:SAMe is from about 1:4 to 1:64. In some embodiments, provided herein are compositions comprising exogenous SAMe and propyl gallate, wherein the weight ratio of propyl gallate:SAMe is from about 1:1 to 1:16. In some embodiments, the gallic acid ester is propyl gallate and the weight ratio of propyl gallate:SAMe is from 1:1 to 1:2, 1:2 to 1:3, 1:3 to 1:4, 1:4 to 1:5, 1:5 to 1:6, 1:6 to 1:7, 1:7 to 1:8, 1:8 to 1:9, 1:9 to 1:10, 1:10 to 1:11, 1:11 to 1:12, 1:12 to 1:13, 1:13 to 1:14, 1:14 to 1:15, or 1:15 to 1:16. In some embodiments, the gallic acid ester is propyl gallate and the weight ratio of propyl gallate:SAMe is about 1:16.

In some embodiments, provided herein are compositions comprising exogenous SAMe and propyl gallate, wherein the weight ratio of propyl gallate:SAMe is from about 1:4 to 1:64.

In some embodiments, the ratio (weight:weight) of said gallic acid ester to S-adenosylmethionine is from 1:1 to 1:64.

In some embodiments, the ratio (weight:weight) of said gallic acid ester to S-adenosylmethionine is from 1:1 to 1:16.

In some embodiments, provided herein are formulations comprising exogenous SAMe and one or more gallic acid ester, comprising about 1 to about 200 mg of gallic acid ester. In some embodiments, said formulations comprise about 1 to about 150 mg of gallic acid ester. In some embodiments, said formulations comprise about 5 to about 100 mg of gallic acid ester. In some embodiments, said formulations comprise about 1 to about 5 mg of gallic acid ester. In some embodiments, said formulations comprise about 5 to about 10 mg, about 10 to about 50 mg, about 50 to about 100 mg, about 100 to about 150 mg, about 150 to about 200 mg, about 200 to about 250 mg, about 250 to about 300 mg, about 300 to about 350 mg, about 350 to about 400 mg or greater than about 400 mg gallic acid ester.

In some embodiments, said formulations comprise about 1 to about 100 mg of gallic acid ester.

In some embodiments, said formulations comprise about 1 to about 50 mg of gallic acid ester.

In some embodiments, said formulations comprise about 10 to about 50 mg of gallic acid ester.

In some embodiments, said formulations comprise about 25 mg of gallic acid ester.

In some embodiments, provided herein are compositions and formulations comprising exogenous SAMe and one or more gallic acid ester, wherein said composition comprises 0.1 to 80% by weight gallic acid ester. In some embodiments, said compositions or formulations comprise 0.1 to 70% by weight gallic acid ester. In some embodiments, said compositions or formulations comprise 0.1 to 60% by weight gallic acid ester. In some embodiments, said compositions or formulations comprise 0.1 to 50% by weight gallic acid ester. In some embodiments, said compositions or formulations comprise 0.1 to 40% by weight gallic acid ester. In some embodiments, said compositions or formulations comprise 0.1 to 30% by weight gallic acid ester. In some embodiments, said compositions or formulations comprise 0.1 to 20% by weight gallic acid ester. In some embodiments, said compositions or formulations comprise 0.1 to 10% by weight gallic acid ester. In some embodiments, said compositions or formulations comprise 0.5 to 10% by weight gallic acid ester. In some embodiments, said compositions or formulations comprise 0.5 to 5% by weight gallic acid ester. In some embodiments, said compositions or formulations comprise 0.5 to 2.5% by weight gallic acid ester. Other exemplary embodiments comprise from 0.25 to 1%, 1 to 2%, 2 to 3%, 3 to 4%, 4 to 5%, 5 to 10%, 10 to 15%, 15 to 20%, 20 to 25%, 25 to 30%, 30 to 35%, 35 to 40%, 40 to 50%, 50 to 60%, 60 to 70%, 70 to 80% or greater than 80% by weight gallic acid ester. The percentage by weight is based on the weight of the total dosage form.

In some embodiments, said compositions or formulations comprise 0.5 to 5% by weight gallic acid ester.

In some embodiments, said compositions or formulations comprise 0.5 to 2.5% by weight gallic acid ester.

In some embodiments, provided herein are compositions and formulations comprising exogenous SAMe and one or more gallic acid ester, comprising about 10 to about 1200 mg of SAMe. In some embodiments, said compositions or formulations comprise about 100 to about 1000 mg of SAMe. In some embodiments, said compositions or formulations comprise about 100 to about 800 mg of SAMe. In some embodiments, said compositions or formulations comprise about 100 to about 600 mg of SAMe. In some embodiments, said compositions or formulations comprise about 100 to about 500 mg of SAMe. In some embodiments, said compositions or formulations comprise about 100 to about 400 mg of SAMe.

In some embodiments, said compositions or formulations comprise about 100 mg of SAMe. In some embodiments, said compositions or formulations comprise about 200 mg of SAMe. In some embodiments, said compositions or formulations comprise about 400 mg of SAMe. In some embodiments, said compositions or formulations comprise about 600 mg of SAMe. In some embodiments, said compositions or formulations comprise about 800 mg of SAMe. In some embodiments, said compositions or formulations comprise about 1000 mg of SAMe. In some embodiments, said compositions or formulations comprise about 1200 mg of SAMe. In some embodiments, said compositions or formulations comprise about 1600 mg of SAMe. In some embodiments, said compositions or formulations comprise about 3200 mg of SAMe. In some embodiments, said compositions or formulations comprise about 3600 mg of SAMe. When referring to the amount of SAMe it is intended to mean the SAMe ion.

In some embodiments, said compositions or formulations comprise about 400 mg of SAMe.

In some embodiments, provided herein are compositions and formulations comprising exogenous SAMe and one or more gallic acid ester, wherein said composition comprises at least 10% by weight SAMe. In some embodiments, said compositions or formulations comprise at least 20% by weight SAMe. In some embodiments, said compositions or formulations comprise at least 30% by weight SAMe. In some embodiments, said compositions or formulations comprise at least 40% by weight SAMe. In some embodiments, said compositions or formulations comprise at least 50% by weight SAMe. In some embodiments, said compositions or formulations comprise at least 60% by weight SAMe. In some embodiments, said compositions or formulations comprise at least 70% by weight SAMe. In some embodiments, said compositions or formulations comprise at least 80% by weight SAMe. In some embodiments, said compositions or formulations comprise at least 90% by weight SAMe. In some embodiments, said compositions or formulations comprise from about 10 to 90% by weight SAMe. In some embodiments, said compositions or formulations comprise from about 20 to 80% by weight SAMe. In some embodiments, said compositions or formulations comprise from about 30 to 70% by weight SAMe. In some embodiments, said compositions or formulations comprise from about 30 to 60% by weight SAMe. In some embodiments, said compositions or formulations comprise from about 30 to 50% by weight SAMe. In some embodiments, said compositions or formulations comprise from about 30 to 40% by weight SAMe. When referring to the percent by weight of SAMe it is intended to mean the SAMe ion.

In some embodiments, SAMe is a SAMe disulfate tosylate salt or a SAMe 1,4-butanedisulfonate salt.

In preferred embodiments, SAMe is a SAMe disulfate tosylate salt.

In some embodiments, provided herein are compositions which provide increased plasma SAMe levels. In some embodiments, the composition when administered to a selected subject group provides in said selected subject group an average maximum SAMe blood plasma concentration (average $C_{max}$) of at least about 120 ng/mL per each 100 mg of SAMe ion, or of at least about 130 ng/mL per each 100 mg of SAMe ion, or of at least about 150 ng/mL per each 100 mg of SAMe ion, or of at least about 175 ng/mL per each 100 mg of SAMe ion, or of at least about 200 ng/mL per each 100 mg of SAMe ion, or of at least about 225 ng/mL per each 100 mg of SAMe ion or of at least about 250 ng/mL per each 100 mg of SAMe ion, or of at least about 300 ng/mL per each 100 mg of SAMe ion. In some embodiments, the composition when administered to a selected subject group provides in said selected subject group an average SAMe $C_{max}$ of at least about 120 ng/mL per each 100 mg of SAMe ion. In some embodiments, the composition when administered to a selected subject group provides in said selected subject group an average SAMe $C_{max}$ of at least about 130 ng/mL per each 100 mg of SAMe ion. In some embodiments, the composition when administered to a selected subject group provides in said selected subject group an average SAMe $C_{max}$ of at least about 135 ng/mL per each 100 mg of SAMe ion. In some embodiments, the composition when administered to a selected subject group provides in said selected subject group an average SAMe $C_{max}$ of at least about 140 ng/mL per each 100 mg of SAMe ion. In some embodiments, the composition when administered to a selected subject group provides in said selected subject group an average SAMe $C_{max}$ of at least about 145 ng/mL per each 100 mg of SAMe ion.

In some embodiments, the composition when administered to a selected subject group provides in said selected subject group an average maximum SAMe blood plasma concentration (average $C_{max}$) of at least about 120 ng/mL per each 100 mg of SAMe ion.

In some embodiments, the composition when administered to a selected subject group provides in said selected subject group an average SAMe $C_{max}$ of at least about 12 ng/mL, at least about 13 ng/mL, at least about 15 ng/mL, at least about 17.5 ng/mL, at least about 20 ng/mL, at least about 22.5 ng/mL, at least about 25 ng/mL, or at least about 30 ng/mL per each 10 mg of SAMe ion. In other embodiments, the composition when administered to a selected subject group provides in said selected subject group an average SAMe $C_{max}$ of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In some embodiments, the composition when administered to a selected subject group provides in said selected subject group an average SAMe $C_{max}$ of at least about 12 ng/mL per each 1 mg of SAMe ion. In some embodiments, the composition when administered to a selected subject group provides in said selected subject group an average SAMe $C_{max}$ of at least about 13 ng/mL per each 1 mg of SAMe ion. In some embodiments, the composition when administered to a selected subject group provides in said selected subject group an average SAMe $C_{max}$ of at least about 14 ng/mL per each 1 mg of SAMe ion. In some embodiments, the composition when administered to a selected subject group provides in said selected subject group an average SAMe $C_{max}$ of at least about 14.5 ng/mL per each 1 mg of SAMe ion.

In some embodiments, the composition when administered to a selected subject group provides in said selected subject group an average SAMe $C_{max}$ of at least about 12 ng/mL per each 10 mg of SAMe ion.

In preferred embodiments, the gallic acid ester is propyl gallate. In some embodiments, provide herein are compositions comprising SAMe and propyl gallate, wherein said compositions when administered to a selected subject group provides in said selected subject group an average SAMe $C_{max}$ of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 12 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 13 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 14 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 14.5 ng/mL per each 1 mg of SAMe ion.

In some embodiments, provide herein are compositions comprising SAMe and propyl gallate, wherein said compositions when administered to a selected subject group provides in said selected subject group an average SAMe $C_{max}$ of at least about 1.2 ng/mL per each 1 mg of SAMe ion.

In some embodiments, provided herein are compositions which when administered to a selected subject group provides in said selected subject group an average AUC of at least about 800 ng·h/mL per each 100 mg dosage of SAMe ion, or of at least about 850 ng·h/mL per each 100 mg dosage of SAMe ion, or at least about 900 ng·h/mL per each 100 mg dosage of SAMe ion, at least about 950 ng·h/mL per each 100 mg dosage of SAMe ion, or at least about 1000 ng·h/mL per each 100 mg dosage of SAMe ion. In some embodiments, the compositions when administered to a selected subject group provides in said selected subject group an average AUC of at least about 800 ng·h/mL per each 100 mg dosage of SAMe ion. In some embodiments, the compositions when administered to a selected subject group provides in said selected subject group an average AUC of at least about 850 ng·h/mL per each 100 mg dosage of SAMe ion. In some embodiments, the compositions when administered to a selected subject group provides in said selected subject group an average AUC of at least about 900 ng·h/mL per each 100 mg dosage of SAMe ion. In some embodiments, the compositions when administered to a selected subject group provides in said selected subject group an average AUC of at least about 950 ng·h/mL per each 100 mg dosage of SAMe ion. In some embodiments, the compositions when administered to a selected subject group provides in said selected subject group an average AUC of at least about 1000 ng·h/mL per each 100 mg dosage of SAMe ion.

In some embodiments, provided herein are compositions which when administered to a selected subject group provides in said selected subject group an average AUC of at least about 800 ng·h/mL per each 100 mg dosage of SAMe ion.

In some embodiments, the composition when administered to a selected subject group provides in said selected subject group an average SAMe AUC of at least about 80 ng·h/mL, at least about 85 ng·h/mL, at least about 90 ng·h/mL, at least about 95 ng·h/mL, or at least about 100 ng·h/mL per each 10 mg of SAMe ion.

In some embodiments, the composition when administered to a selected subject group provides in said selected subject group an average SAMe AUC of at least about 80 ng·h/mL per each 10 mg of SAMe ion.

In other embodiments, the composition when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, the compositions when administered to a selected subject group provides in said selected subject group an average AUC of at least about 8 ng·h/mL per each 1 mg dosage of SAMe ion. In some embodiments, the compositions when administered to a selected subject group provides in said selected subject group an average AUC of at least about 8.5 ng·h/mL per each 1 mg dosage of SAMe ion. In some embodiments, the compositions when administered to a selected subject group provides in said selected subject group an average AUC of at least about 9 ng·h/mL per each 1 mg dosage of SAMe ion. In some embodiments, the compositions when administered to a selected subject group provides in said selected subject group an average AUC of at least about 9.5 ng·h/mL per each 1 mg dosage of SAMe ion. In some embodiments, the compositions when administered to a selected subject group provides in said selected subject group an average AUC of at least about 10 ng·h/mL per each 1 mg dosage of SAMe ion.

In other embodiments, the composition when administered to a selected subject group provides in said selected subject group an average SAMe AUC of at least about 8 ng·h/mL per each 1 mg of SAMe ion.

In preferred embodiments, the gallic acid ester is propyl gallate. In some embodiments, provide herein are compositions comprising SAMe and propyl gallate, wherein said compositions when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, provide herein are compositions comprising SAMe and propyl gallate, wherein said compositions when administered to a selected subject group provides in said selected subject group an average AUC of at least about 8 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 8.5 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 9 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 9.5 ng·h/mL per each 1 mg dosage of SAMe ion. In embodiments, provide herein are compositions comprising SAMe and propyl gallate, wherein said compositions when administered to a selected subject group provides in said selected subject group an average AUC of at least about 10 ng·h/mL per each 1 mg dosage of SAMe ion.

In some embodiments, provide herein are compositions comprising SAMe and propyl gallate, wherein said compositions when administered to a selected subject group provides in said selected subject group an average SAMe AUC of at least about 8 ng·h/mL per each 1 mg of SAMe ion.

In some embodiments, the exogenous SAMe ion dose administered is at least 10 mg. In some embodiments, the exogenous SAMe ion dose administered is from 10 to 3600 mg. In some embodiments, the composition when administered to a selected subject group provides in said selected subject group an average SAMe $C_{max}$ of at least about 120 ng/mL and an average AUC of at least about 800 ng·h/mL per each 100 mg of SAMe ion for doses of SAMe ion of at least 100 mg. In other embodiments, the composition when administered to a selected subject group provides in said selected subject group an average SAMe $C_{max}$ of at least about 130 ng/mL and an average AUC of at least about 850 ng·h/mL per each 100 mg of SAMe ion for doses of SAMe ion of at least 100 mg. In still other preferred embodiments, the composition when administered to a selected subject group provides in said selected subject group an average SAMe $C_{max}$ of at least about 12 ng/mL and an average AUC of at least about 90 ng·h/mL per each 10 mg of SAMe ion for doses of SAMe ion of at least 10 mg. In some embodiments, the composition when administered to a selected subject group provides in said selected subject group an average SAMe $C_{max}$ of at least about 13 ng/mL and an average AUC of at least about 90 ng·h/mL per each 10 mg of SAMe ion for doses of SAMe ion of at least 10 mg. In other embodiments, the composition when administered to a selected subject group provides in said selected subject group an average SAMe $C_{max}$ of at least about 1.2 ng/mL and/or an average AUC of at least about 9 ng·h/mL per each 1 mg of SAMe ion. In some embodiments, the composition when administered to a selected subject group provides in said selected subject group an average SAMe $C_{max}$ of at least about 1.3 ng/mL and/or an average AUC of at least about 9 ng·h/mL per each 1 mg of SAMe ion. In some embodiments, provided herein are compositions comprising SAMe and propyl gallate which when administered to a selected subject group provide in said selected subject group an average SAMe $C_{max}$ of at least about 1.4 ng/mL and/or an average AUC of at least about 9 ng·h/mL per each 1 mg of SAMe ion. In other embodiments, provided herein are compositions comprising SAMe and propyl gallate which when said compositions are administered to a selected subject group provide in said selected subject group an average SAMe Cmax of at least about 1.5 ng/mL and/or an average AUC of at least about 9 ng·h/mL per each 1 mg of SAMe ion. In additional embodiments, provided herein are compositions comprising SAMe and propyl gallate which when said compositions are administered to a selected subject group provide in said selected subject group an average SAMe Cmax of at least about 1.3 ng/mL and/or an average AUC of at least about 9.5 ng·h/mL per each 1 mg of SAMe ion. In other embodiments, provided herein are compositions comprising SAMe and propyl gallate which when said compositions are administered to a selected subject group provide in said selected subject group an average SAMe Cmax of at least about 1.3 ng/mL and/or an average AUC of at least about 10.0 ng·h/mL per each 1 mg of SAMe ion.

In some embodiments, provided herein are compositions which provide in the subject one of an average Tmax or Cmax with reduced variation or a reduced effective dose in comparison to a SAMe control group. SAMe control groups are those wherein the subject or selected subject group is administered the same or similar SAMe formulation with the exception that the one or more gallic acid ester is not present.

In some embodiments, provided herein are compositions which when administered to a selected subject group provide in said selected subject group an improved SAMe pharmacokinetic profile such that once a day dosing using compositions described herein is equivalent (or better) to bi-daily dosing of conventional SAMe compositions that do not contain at least one gallic acid ester. "Improved SAMe pharmacokinetic profile" can be measured by, for example, an equivalent or higher SAMe AUC or Cmax, a reduced variation of SAMe Tmax, a reduced side effect profile, and/or an increased rate of onset. In some embodiments, provided herein are compositions comprising SAMe and propyl gallate wherein once a day administration of said compositions to a selected subject group provides in said selected subject group an improved SAMe pharmacokinetic profile in comparison to a SAMe control group.

In some exemplary embodiments, a functional coating acts to co-deliver exogenous SAMe and the gallic acid ester to the upper small intestine where SAMe is better absorbed. In other embodiments, the functional coating results in delivery of exogenous SAMe and the gallic acid ester to the large intestine and/or colorectal regions.

In certain embodiments, provided herein are compositions comprising a unit dosage form that comprises a functional coating. Preferably, said functional coating constitutes from 1 to 20% of the total weight of the unit dosage form. In some embodiments, said functional coating comprises more than one coating layers. In certain embodiments, said functional coating comprises a seal coat and one or more additional coating layers. Preferably, said one or more additional coating layers is an enteric, time-release, non pH-dependent or pH-dependent coating. In some embodiments, said one or more additional coating layers constitutes at least 3%, 3.5%, 4%, 4.5%, 5%, or 5.5% of the total weight of the unit dosage form. More preferably, said one or more additional coating layers is an enteric coating which constitutes from 3-5% of the total weight of the unit dosage form. Most preferably, provided herein are compositions comprising SAMe and propyl gallate wherein said compositions comprise an enteric, time-release, non pH-dependent or pH-dependent coating which constitutes at least 3%, 3.5%, 4%, 4.5%, 5%, or 5.5% of the total weight of the dosage form.

In some embodiments, the composition provided herein comprises an oral dosage form or delivery system. Preferably, said oral dosage form or delivery system is a capsule or non-capsule. Most preferably, said non-capsule dosage form is a tablet. In other embodiments, the composition comprises a transdermal, transmucosal, or intramuscular dosage form. In some other embodiments, the composition comprises a dosage form for intravenous administration.

In some embodiments, the compositions provided herein comprise a minitablet. "Minitablets" or "mini-tablets" as used herein are tablets of a smaller size, typically <3 mm in diameter. Minitablets contain similar excipients as larger tablets. They are also typically made using methods similar to those used for larger tablets, such as tablet compression, seal coating and enteric coating. In some embodiments, the minitablets are filled into a capsule or pressed gently to form a larger tablet. In some embodiments, the minitablets are filled into a capsule or pressed gently to form a larger tablet along with one or more pH moderator. In some embodiments, the minitablets are filled into a capsule. In some embodiments, the minitablets are pressed into a larger tablet. In some embodiments, the minitablets are pressed into an oral disintegration tablet or "ODT". In some embodiments, the minitablets are used to reduce tablet retention within the stomach. In some embodiments, the minitablets are used to reduce side-effects associated with SAMe counter-ion(s).

In some embodiments, the minitablets are used for administration under fed conditions. In some embodiments, the minitablets are used for administration under fasted conditions. In some embodiments, administration of larger tablets exhibits a postponement in the Tmax of SAMe (or other drugs). In some embodiments, administration of the minitablet composition under fed conditions reduces postponement of the SAMe Tmax. In some embodiments, administration of the minitablet composition under fed conditions reduces retention in the stomach or a delay in gastric emptying.

In some embodiments, the minitablet composition comprises about 10 to 80% SAMe. In some embodiments, the minitablet composition comprises about 10 to 70% SAMe. In some embodiments, the minitablet composition comprises about 10 to 60% SAMe. In some embodiments, the minitablet composition comprises about 10 to 50% SAMe. In some embodiments, the minitablet composition comprises about 15 to 45% SAMe.

In some embodiments, diseases and/or disorders treatable with SAMe and gallic acid ester formulations provided herein are selected from the group consisting of, but not limited to, a mental or psychiatric disorder (e.g. psychotic/mood or non-psychotic mental disorders exemplified by depression and substance related disorders, respectively), a nervous system disease/disorder (e.g. a central nervous system disease exemplified by Alzheimer's), other neurological diseases/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis, a joint disease or disorder which is arthritis or osteoarthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, atherosclerosis, Lesch-Nyhan disease, a metabolic disease/disorder (e.g. Type 2 diabetes) and a disorder induced in whole or in part by oxidative or free-radical damage. In preferred embodiments, the composition comprises SAMe and one of ethyl gallate, isoamyl gallate, propyl gallate or octyl gallate as provided herein. In most preferred embodiments, the composition comprises SAMe and propyl gallate.

Additional embodiments provided herein relate to combinations of exogenous SAMe and one or more gallic acid ester along with one or more active ingredients that are commonly prescribed or used for treatment of and/or prophylaxis of various diseases or disorders in a subject. In preferred embodiments, the composition comprises SAMe and one of ethyl gallate, isoamyl gallate, propyl gallate or octyl gallate as provided herein. In most preferred embodiments, the composition comprises SAMe and propyl gallate.

Also provided herein are methods for treating or preventing and/or prophylaxis in a subject a disease or disorder selected from the group consisting of, but not limited to, a mental or psychiatric disorder (e.g. psychotic/mood or non-psychotic mental disorders exemplified by depression and substance related disorders, respectively), a nervous system disease/disorder (e.g. a central nervous system disease exemplified by Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis, a joint disease or disorder which is arthritis or osteoarthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, atherosclerosis, Lesch-Nyhan disease, and a disorder induced in whole or in part by oxidative or free-radical damage, comprising administering a composition comprising SAMe and one or more gallic acid ester, such that said disease is treated or prevented. In preferred embodiments, the composition comprises SAMe and one of ethyl gallate, isoamyl gallate, propyl gallate or octyl gallate as provided herein. In most preferred embodiments, the composition comprises SAMe and propyl gallate. Preferably, said disease or disorder is depression. Even more preferably, said depression is Major depressive disorder (also known as Major depression, Clinical depression), Dysthymic disorder (or also referred to as Dysthymia), Bipolar disorder (formerly referred to as Manic depression), Postpartum depression, Seasonal Affective Disorder (SAD), Anxiety depression, Atypical depression, Melancholic depression, Catatonic depression and Situational depression, Reactive depression, Late-Life depression (and the like), Parkinson's depression, HIV-associated depression, brief recurrent depression, Mild depression, Minor depression, Treatment-Resistant depression (TRD), co-morbid depression, or depression NOS (Not Otherwise Specified).

In some embodiments, any of the compositions provided herein is used in the treatment of the diseases and disorders described herein.

Also provided herein are methods for administering a composition comprising SAMe and a gallic acid ester wherein said method comprises administering said composition to a patient or selected subject group that have fasted prior to administration of said composition. "Fasted" typically is meant to be an overnight fast such that patients (or subjects) are administered the composition at least one hour prior to their first meal of the day (i.e. typically breakfast). Preferred "fasted" conditions are such that subjects begin fasting at least 10 or 12 hours before drug administration and fasting continues for 1 or 4 hours following drug administration. Also provided herein are methods for administering a composition comprising SAMe and a gallic acid ester wherein said method comprises administering said composition to a patient or selected subject group under fed conditions. "Fed" conditions are typically such that the patients/subjects ingest a meal approximately 1-2 hours before being administered the composition of the invention. Preferably, under "fed" conditions, subjects start fasting at least 12 hours before morning breakfast and then receive a meal (often a standardized high-fat, high-calorie meal) approximately 30 minutes before drug administration.

In some embodiments, compositions and formulations provided herein exhibit little to no gender-based pharmacokinetic effects. After administration of exogenous SAMe using formulations previously reported in the art, some of the effects of SAMe have been reported to be different in males and females. There are numerous theories regarding the reason for these gender effects. Surprisingly, compositions and formulations provided herein exhibit pharmacokinetic profiles in which there is no statistically significant difference in values between males and females. In some embodiments, provided herein are compositions and formulations which exhibit pharmacokinetic profiles that are similar in both males and females.

Also provided herein are methods for improving the uptake of SAMe, wherein said method comprises administering to a subject an exemplary composition which provides a physiologically effective amount of exogenous SAMe in combination with one or more gallic acid ester. Preferably said gallic acid ester is selected from ethyl gallate, isoamyl gallate, propyl gallate or octyl gallate. Most preferably, said gallic acid ester is propyl gallate.

Further provided herein is a method of making a formulation for improved uptake of SAMe, wherein said method comprises mixing exogenous SAMe and a gallic acid ester and formulating them into a capsule or non-capsule with or without additional excipients. Preferably said gallic acid ester is selected from ethyl gallate, isoamyl gallate, propyl gallate or octyl gallate. Most preferably, said gallic acid ester is propyl gallate.

Thus in some embodiments, provided herein is a method for improving the uptake of SAMe, wherein said method comprises administering to said subject an exemplary composition which provides a physiologically effective amount of exogenous SAMe in combination with propyl gallate. Also provided in some embodiments is a method of making a formulation for improved uptake of SAMe, wherein said method comprises combining exogenous SAMe and propyl gallate and formulating them into a capsule or non-capsule with or without additional excipients. In other embodiments, provided is a method of administering a composition comprising exogenous SAMe and propyl gallate wherein said method comprises administering said composition to a patient that has fasted for at least 10 hours prior to administration of said composition.

The details of one or more embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

Figure 1:
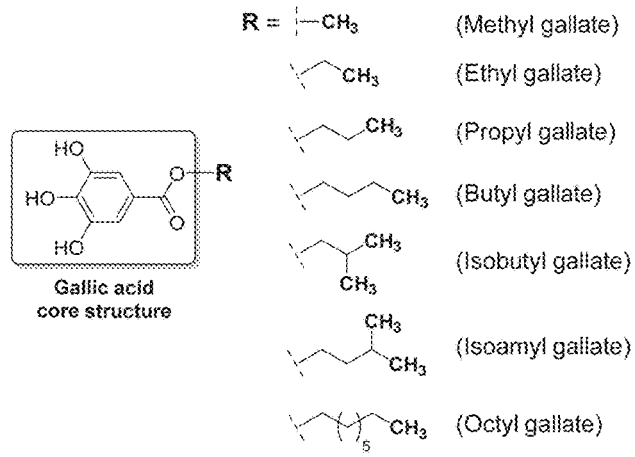
FIG. 1 is a graph of the average maximum SAMe plasma concentration (Cmax) of beagles administered a single 400 mg SAMe ion dose from one of ten different formulations: (1) a commercially available oral formulation of SAMe, (2) MSI SAMe formulation with no propyl gallate ("Control SAMe"); (3) MSI SAMe formulation co-administered with a separate 25 mg propyl gallate tablet ("Control SAMe with Separate PG"); (4) MSI SAMe formulation co-formulated with 25 mg methyl gallate; (5) MSI SAMe formulation co-formulated with 25 mg ethyl gallate; (6) MSI SAMe formulation co-formulated with 25 mg propyl gallate; (7) MSI SAMe formulation co-formulated with 25 mg butyl gallate; (8) MSI SAMe formulation co-formulated with 25 mg isobutyl gallate; (9) MSI SAMe formulation co-formulated with 25 mg isoamyl gallate; or (10) MSI SAMe formulation co-formulated with 25 mg octyl gallate.
Figure 1:
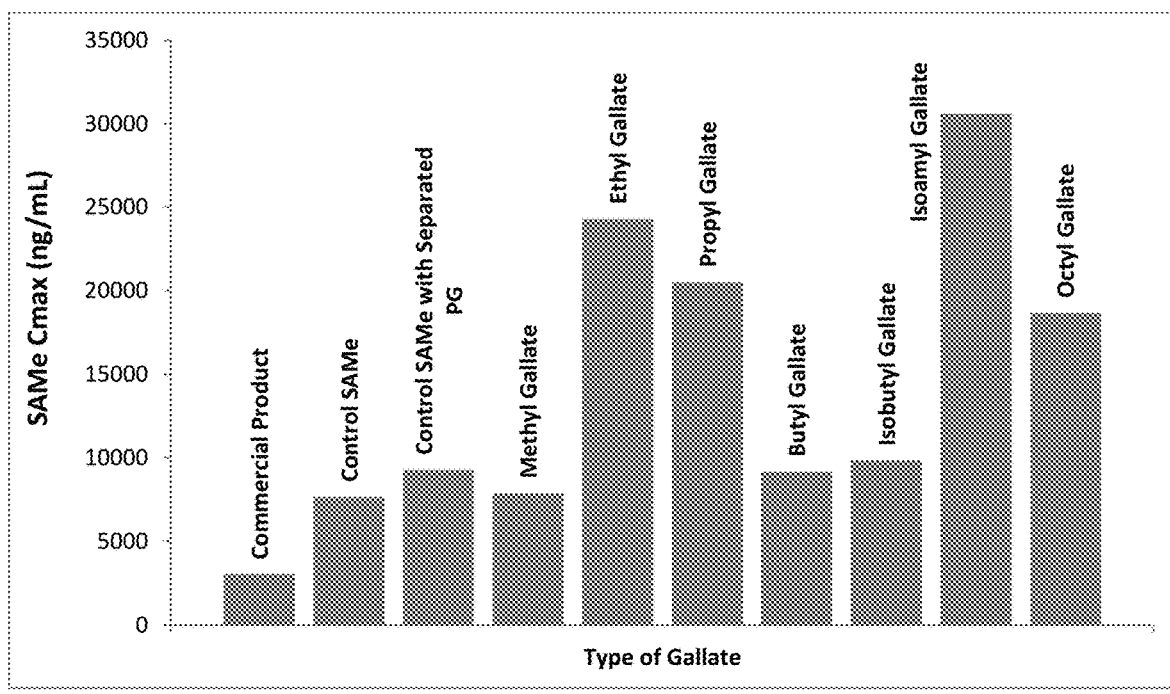

The present investigators have surprisingly discovered that the delivery of exogenous SAMe can be significantly improved when at least one gallic acid ester is administered in combination with exogenously supplied SAMe. Thus some embodiments relate to formulations comprising SAMe and one or more gallic acid ester. Other embodiments relate to compositions and methods that improve the uptake of exogenous SAMe and methods of using the same, e.g. for the treatment of various diseases or disorders in a subject and/or improving the nutritional status of a subject. Additional embodiments relate to combinations of SAMe and one or more gallic acid ester with one or more active ingredients that are commonly prescribed or used for treatment of and/or prophylaxis of various diseases or disorders in a subject. While not wishing to be bound by any one specific embodiment, provided herein is a method of increasing the absorption of SAMe wherein said one or more gallic acid ester binds to and/or interacts with said SAMe and/or the gastrointestinal tract in such a way as to increase SAMe absorption across the mucosal wall or epithelial cells of the intestine.

As used herein the term "SAMe" refers to S-adenosyl-L-methionine (or, more simply, "S-adenosylmethionine") including all of the various SAMe salts. When referring to dose or percentage, the amount (typically in mg) refers to the dose of SAMe ion administered. As mentioned above, SAMe is most commonly available as a stable salt form, e.g. with p-toluenesulfonic acid (see U.S. Pat. No. 3,893,999, incorporated herein by reference in its entirety). Other stable SAMe salts are described in, for example, U.S. Pat. No. 5,128,249, which describes particular stable salts of SAMe. Various morphologies of SAMe are suitable for use in certain embodiments provided herein. Thus, as used herein "SAMe" refers to the stable salts, amorphous forms, semicrystalline forms and crystalline forms of SAMe as well as to the ionic form of SAMe when present in vivo. Amorphous forms of SAMe can be employed at any particle size and particle size distribution.

Formulations for oral administration of exogenous SAMe are typically provided as solid or semi-solid products, dosage forms or oral delivery systems, exemplified by capsules or non-capsule dosage forms which include tablets, lozenges, gum, pastes, pellets, or granules, and generally consist of a core "matrix material" as well as one or more coatings. "Product" or "dosage form" or "oral delivery system" as used herein refers to any solid or semi-solid formulation or preparation used for oral administration and is exemplified by capsules, tablets, pastes, granules, caplets, lozenges and the like; all of which are well-known and well-documented in the art. These formulations may be administered using a clinical, pharmaceutical or veterinary dosing regimen. Oral dosage forms may also be provided as dietary or nutritional supplements or as a medical food.

"Gallates", "alkyl gallates" or "gallic acid esters" as used herein refer to salts and esters of gallic acid and have the general formula I (see below) where $R_1$ is a hydrocarbon chain which may be straight or branched. Optionally, $R_1$ group may be an alkyl, alkenyl, alkynyl, aryl, benzyl, phenyl, alicyclic, or heterocyclic group all of which groups may be substituted or unsubstituted. $R_1$ is preferably a $C_1$-$C_{22}$ alkyl group, a $C_2$-$C_{22}$ alkenyl group or a $C_2$-$C_{22}$ alkynyl group, all of which groups may be substituted or unsubstituted and may be straight chain, cyclic, cyclic unsaturated or branched chain. Moreover, this hydrocarbon chain can be a saturated, monounsaturated, or polyunsaturated. Preferably, $R_1$ is a saturated hydrocarbon chain ranging from $C_1$-$C_{22}$.

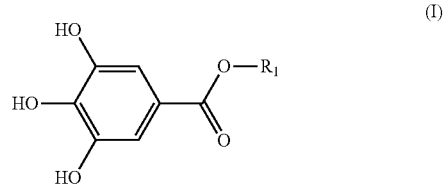

(I)

Preferred gallic acid esters for use in the invention are methyl gallate, ethyl gallate, propyl gallate, iso-propyl gallate, butyl gallate, isobutyl gallate, amyl gallate, isoamyl gallate, hexyl gallate, isohexyl gallate, heptyl gallate, isoheptyl gallate, octyl gallate, isooctyl gallate, nonyl gallate, isononyl gallate, decyl isodecyl, undecyl gallate, isoundecyl gallate, dodecyl gallate (lauryl gallate), isododecyl gallate, tridecyl gallate, isotridecyl, tetradecyl gallate, isotetradecyl gallate, pentadecyl gallate, isopentadecyl gallate, hexadecyl gallate (cetyl gallate), isohexadecyl gallate, heptadecyl gallate, isoheptadecyl gallate, octadecyl gallate, isoctadecyl gallate, cis-9-hexadecenyl (palmitoleyl) gallate, cis-9-octadecenyl (oleyl) gallate, cis,cis-9,12 octadecadienyl (linoleyl) gallate, trans,trans-9,12-octadecadienyl (linolelaidyl) gallate, cis,cis,cis-9,12,15-octadecatrienyl (linolenyl) gallate, trans,trans,trans-9,12,15-octadecatrienyl (linolenelaidyl) gallate, cis,cis,cis-6,9,12-octadecatrienyl (gamma-linolenyl) gallate, trans 9-octadecenyl (elaidyl) gallate or trans-9-hexadecenyl (palmitelaidyl) gallate. catechin gallate, epicatechin gallate, gallocatechin gallate, epigallocatechin gallate, gallocatechol gallate, 2-ethylhexyl gallate, 2-hydroxyethyl gallate, 6-O-galloylglucose, hamamelitannin, methoxyethoxyethoxyethyl m-digallate, theaflavin monogallate A &B, theaflavin digallate. More preferably, the gallic acid ester is selected from ethyl gallate, isoamyl gallate, propyl gallate or octyl gallate. Even more preferably, the gallic acid ester is considered a GRAS (Generally Recognized As Safe) substance by the U.S. Food and Drug Administration (FDA). Also preferably, the gallic acid ester has received a Novel Food approval by either the European Food Safety Authority (EFSA) or the European Medicines Agency (EMA). Most preferably, the gallic acid ester is propyl gallate. Thus provided herein are formulations comprising SAMe and propyl gallate. Propyl gallate is a preferred gallic acid ester as the investigators have shown for the first time that propyl gallate has a dose-response relationship with SAMe uptake in vivo.

In certain exemplary embodiments, the ratio (weight:weight) of gallic acid ester to exogenous SAMe is from 5:1 to 1:400. Preferably, the ratio (weight:weight) of gallic acid ester to S-adenosylmethionine is from 5:1 to 1:100, from 4:1 to 1:80, or from 1:1 to 1:16. In some preferred embodiments, the gallic acid ester is ethyl gallate, isoamyl gallate or octyl gallate and the weight ratio of ethyl gallate, isoamyl gallate or octyl gallate to SAMe is from 1:1 to 1:16. Within various embodiments, the gallic acid ester is propyl gallate and the weight ratio of propyl gallate:SAMe is from 1:1 to 1:100. In some preferred embodiments, the gallic acid ester is propyl gallate and the weight ratio of propyl gallate:SAMe is from 1:1 to 1:16. In more preferred embodiments, the gallic acid ester is propyl gallate and the weight ratio of propyl gallate:SAMe is from 1:1 to 1:2, 1:2 to 1:3, 1:3 to 1:4, 1:4 to 1:5, 1:5 to 1:6, 1:6 to 1:7, 1:7 to 1:8, 1:8 to 1:9, 1:9 to 1:10, 1:10 to 1:11, 1:11 to 1:12, 1:12 to 1:13, 1:13 to 1:14, 1:14 to 1:15, or 1:15 to 1:16. Most preferably, the gallic acid ester is propyl gallate and the weight ratio of propyl gallate:SAMe is about 1:16. Thus in some embodiments, provided is a composition comprising SAMe and propyl gallate wherein the weight ratio of propyl gallate:SAMe is from 1:1 to 1:16. Thus in some other embodiments, provided is a composition comprising SAMe and propyl gallate wherein the weight ratio of propyl gallate:SAMe is about 1:16.

In some embodiments, said composition comprising exogenous SAMe and gallic acid ester comprises from about 1 to about 5 mg, or about 5 to about 10 mg of gallic acid ester. Some other exemplary embodiments comprise about 10-50 mg gallic acid ester. Other exemplary embodiments comprise from about 50 to about 100 mg, about 100 to about 150 mg, about 150 to about 200 mg, about 200 to about 250 mg, about 250 to about 300 mg, about 300 to about 350 mg, or about 350 to about 400 mg gallic acid ester. Preferred exemplary embodiments comprise from about 5-100 mg of ethyl gallate, isoamyl gallate, propyl gallate or octyl gallate. More preferred exemplary embodiments comprise from about 5-100 mg of propyl gallate. Most preferably, compositions of the invention are administered such that the daily amount of propyl gallate dosed does not exceed the acceptable daily intake ("ADI") for propyl gallate as established by the Joint FAO/WHO Expert Committee on Food Additives (JECFA).

In some embodiments, said composition comprising exogenous SAMe and gallic acid ester comprises from 0.25 to 1%, 1 to 2%, 2 to 3%, 3 to 4%, 4 to 5%, 5 to 6% or 6 to 7% by weight gallic acid ester wherein the weight percentage is based on the weight of the total dosage form. In some other exemplary embodiments, said composition comprising SAMe and a gallic acid ester comprises 7 to 10%, 10 to 15%, 15 to 20%, 20 to 25%, 25 to 30%, 30 to 35%, 35 to 40%, 40 to 50%, 50 to 60%, 60 to 70%, 70 to 80%, or greater than 80% by weight gallic acid ester.

Some exemplary embodiments relate to "low-dose" SAMe compositions. By increasing the uptake of exogenous SAMe in the presence of a gallic acid ester, the daily administered effective dose of SAMe may be substantially lowered by administration of compositions with improved SAMe uptake in comparison to control formulations that do not contain at least one gallic acid ester. These exemplary "low-dose" treatments may enable a lower daily pill count though achieve the same or better pharmacokinetics in comparison to previously available SAMe products administered on a bi-daily or greater schedule. Some embodiments relate to administration of a selected improved dosage on a once-a-day basis. In some embodiments, the once-a-day dose may be administered in a single dosage unit exemplified by, a single tablet, capsule, or caplet. In other exemplary embodiments, the single dose may be administered as multiple tablets, capsules or caplets taken at one time. In some embodiments, for instance, a dosage of about 400 to 3600 mg of SAMe ion per day may be divided into two, three, four or more tablets, capsules or caplets of about 50 to 2000 mg, preferably about 100 to 1600 mg of SAMe per unit. In some preferred embodiments, the daily dose may comprise two, three or four units (e.g. tablets, capsules or caplets) of about 100 to 800 mg of SAMe ion per unit. Suitable dosage regimens included are: four units of about 50-400 mg of SAMe ion per unit, e.g. 50, 100, 150, 200, 250, 300, 350 or 400 mg SAMe ion per unit; three units of about 50-1000 mg of SAMe ion per unit, e.g. 50, 100, 150, 200, 250, 300, 350, 400, 450, 500, 550, 600, 650, 700, 750, 800, 850, 900, 950 or 1,000 mg of SAMe ion per unit; two units of about 50-1600 mg of SAMe ion per unit, e.g. about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or 1600 mg of SAMe ion per unit.

SAMe exemplary formulations comprising a gallic acid ester may be configured to enable high bioavailability of the exogenous SAMe. "High bioavailability" formulations are those which provide higher average maximum SAMe blood plasma concentration (Cmax) and/or average SAMe plasma area under the curve (AUC) values in comparison to the same dosage forms of SAMe without the gallic acid ester or in comparison to other currently available commercial SAMe formulations. High bioavailability formulations when dosed to a selected subject group provide an average Cmax of at least about 100 to 130 ng/mL (and/or an average AUC of at least about 500 ng·h/mL) per each 100 mg dosage of SAMe ion. Thus in some preferred embodiments, SAMe formulations comprising one or more gallic acid ester are provided in high bioavailability SAMe formulations.

Thus, in some exemplary embodiments, the composition when administered to a selected subject group provides in said selected subject group an average SAMe Cmax (average maximum plasma concentration) of at least about 100 ng/mL per each 100 mg of SAMe ion, at least about 110 ng/mL per each 100 mg of SAMe ion, or or at least about 120 ng/mL per each 100 mg of SAMe ion, or of at least about 130 ng/mL per each 100 mg of SAMe ion, or of at least about 150 ng/mL per each 100 mg of SAMe ion, or of at least about 175 ng/mL per each 100 mg of SAMe ion, or of at least about 200 ng/mL per each 100 mg of SAMe ion, or of at least about 225 ng/mL per each 100 mg of SAMe ion or of at least about 250 ng/mL per each 100 mg of SAMe ion, or of at least about 300 ng/mL per each 100 mg of SAMe ion. In some embodiments, the composition when administered to a selected subject group provides in said selected subject group an average SAMe Cmax of at least about 12 ng/mL, at least about 13 ng/mL, at least about 15 ng/mL, at least about 17.5 ng/mL, at least about 20 ng/mL, at least about 22.5 ng/mL, at least about 25 ng/mL, or at least about 30 ng/mL per each 10 mg of SAMe ion. In other embodiments, the composition when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In preferred embodiments, the gallic acid ester is propyl gallate. Thus provide herein are compositions comprising SAMe and propyl gallate, wherein said compositions when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion.

In some embodiments, the composition when administered to a selected subject group provides in said selected subject group an average AUC of at least about 800 ng·h/mL per each 100 mg dosage of SAMe ion, or of at least about 850 ng·h/mL per each 100 mg dosage of SAMe ion, or at least about 900 ng·h/mL per each 100 mg dosage of SAMe ion, at least about 950 ng·h/mL per each 100 mg dosage of SAMe ion, or at least about 1000 ng·h/mL per each 100 mg dosage of SAMe ion. In some embodiments, the composition when administered to a selected subject group provides in said selected subject group an average SAMe AUC of at least about 80 ng·h/mL, at least about 85 ng·h/mL, at least about 90 ng·h/mL, at least about 95 ng·h/mL, or at least about 100 ng·h/mL per each 10 mg of SAMe ion. In other embodiments, the composition when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In preferred embodiments, the gallic acid ester is propyl gallate. Thus provide herein are compositions comprising SAMe and propyl gallate, wherein said compositions when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, the dose of SAMe ion delivered is at least 10 mg. In preferred embodiments, the dose of SAMe ion delivered is from 10 to 1600 mg.

In some embodiments, the term "selected subject group" is a group of selected human subjects. In some embodiments, a suitable "selected subject group" has six or more subjects who are dosed fasted. In some embodiments, all members of the "selected subject group" have pharmacokinetic parameters for SAMe that fall within statistically normal ranges (i.e. no outliers) and no member will be included on the basis of non-standard or unusual SAMe absorption or metabolism. In some embodiments, all members of the "selected subject group" are males. In other embodiments, the selected subject group is a group of selected non-human subjects. Preferably the non-human subjects are major food animals, companion animals or minor species animals. By "companion animals" it is meant to include animals such as, but not limited to, horses, dogs, and cats as recommended by the FDA. In some preferred embodiments, the composition when administered to a selected non-human subject group provides in said selected non-human subject group an average SAMe Cmax of at least about 1000 ng/mL, at least about 1500 ng/mL, at least about 2000 ng/mL, at least about 2500 ng/mL, at least about 3000 ng/mL, or at least about 3500 ng/mL per each 100 mg of SAMe ion. Thus provided herein are compositions comprising SAMe and propyl gallate, wherein administration of said compositions to a selected non-human subject group provides in said selected non-human subject group an average SAMe Cmax of at least about 1000 ng/mL, at least about 1500 ng/mL, at least about 2000 ng/mL, at least about 2500 ng/mL, at least about 3000 ng/mL, or at least about 3500 ng/mL per each 100 mg of SAMe ion.

In other preferred embodiments, the composition when administered to a selected subject group provides in said selected subject group an average SAMe Cmax of at least about 120 ng/mL and an average AUC of at least about 800 ng·h/mL per each 100 mg of SAMe ion for doses of SAMe ion of at least 100 mg. In some other preferred embodiments, the composition when administered to a selected subject group provides in said selected subject group an average SAMe Cmax of at least about 130 ng/mL and an average AUC of at least about 800 ng·h/mL per each 100 mg of SAMe ion for doses of SAMe ion of at least 100 mg. In still other preferred embodiments, the composition when administered to a selected subject group provides in said selected subject group an average SAMe Cmax of at least about 12 ng/mL and an average AUC of at least about 80 ng·h/mL per each 10 mg of SAMe ion for doses of SAMe ion of at least 10 mg. In some other preferred embodiments, the composition when administered to a selected subject group provides in said selected subject group an average SAMe Cmax of at least about 13 ng/mL and an average AUC of at least about 80 ng·h/mL per each 10 mg of SAMe ion for doses of SAMe ion of at least 10 mg. In other preferred embodiments, the composition when administered to a selected subject group provides in said selected subject group an average SAMe Cmax of at least about 1.2 ng/mL and/or an average AUC of at least about 8 ng·h/mL per each 1 mg of SAMe ion. In some other preferred embodiments, the composition when administered to a selected subject group provides in said selected subject group an average SAMe Cmax of at least about 1.3 ng/mL and/or an average AUC of at least about 8 ng·h/mL per each 1 mg of SAMe ion. In some embodiments, the dose of SAMe ion delivered is at least 10 mg. In preferred embodiments, the dose of SAMe ion delivered is from 10 to 3600 mg.

SAMe exemplary formulations comprising a gallic acid ester may also be configured to enable extended release of the formulated SAMe. Co-owned U.S. patent application 2009/0088404, which is incorporated herein by reference, provides novel formulations of extended-release SAMe formulations.

In some preferred embodiments, the composition comprises an oral delivery system, or a transdermal or transmucosal delivery system. In some embodiments, the composition comprises one of capsules or non-capsules (such as tablets, pastes, granules, caplets, lozenges, pastes, patches and suppositories). In some embodiments, the composition is a dietary or nutritional supplement. In some embodiments, the composition is a medical food.

In some exemplary embodiments, the composition is in a dosage form that comprises a functional coating and the functional coating constitutes from 1 to 20% of the total weight of the dosage form. In certain embodiments, the functional coating is comprised of one or more separate coatings or layers. In some embodiments, the one or more separate coatings or layers are each an enteric coating, a time-release coating, a pH-dependent coating, a seal coating or other as well as combinations of these. In preferred embodiments, one or more separate coatings or layers constitutes from 1 to 5%, 2 to 5%, 3 to 5%, or 4 to 5% of the total weight of the dosage form. Most preferably, one or more additional coating layers is an enteric coating which constitutes from 3-5% of the total weight of the unit dosage form.

Preferably, exogenous SAMe and the gallic acid ester are administered at the same time. Even more preferably, SAMe and the gallic acid ester are co-formulated. In some exemplary embodiments, the composition comprises SAMe and a gallic acid ester, wherein said SAMe and gallic acid ester are present in the core of the formulation. In other embodiments, the composition comprises SAMe and a gallic acid ester, wherein said gallic acid ester is present in one or more coating layers of the formulation.

Also provided herein is a method for improving the pharmacokinetic parameters of exogenous SAMe administered to a subject, said method comprising administering to the subject a non-parental composition comprising at least one physiologically effective dosage of SAMe in combination with at least one gallic acid ester selected to improve the pharmacokinetic parameters of said SAMe in a subject, said pharmacokinetic parameters measurable in the subject by one of a Cmax, an AUC, and combinations thereof in comparison to a control group administered the same or similar SAMe formulation yet lacking the gallic acid ester. For greater clarity all references to dose within this patent refer to dose as the dose of SAMe ion. Pharmacokinetic parameters such as average maximum plasma concentration of SAMe (Cmax) are determined using a bioanalytical method with adequate sensitivity, specificity, ruggedness, stability and repeatability (for example, a qualified liquid chromatography triple quad mass spectrometry based method coupled with a suitable extraction method for the separation of analyte from plasma). AUC values are preferably calculated from 0-24 hours using the trapezoid method and are uncorrected for baseline, endogenous SAMe levels. A suitable "selected subject group" or "selected non-human subject group" has six or more subjects. In some embodiments said "selected subject group" or "selected non-human subject group" are dosed fasted (preferably all male subjects). All members of the "selected subject group" or "selected non-human subject group" have pharmacokinetic parameters for SAMe that fall within statistically normal ranges (i.e. no outliers) and no member will be included on the basis of non-standard or unusual SAMe absorption or metabolism which may or may not result from a different genetic profile. The average Cmax values are derived by averaging the concentration at each time point for all members of the subject group. Use of methods in vivo provides superior Cmax and/or AUC values in comparison to conventional dosage forms of SAMe.

Some embodiments also relate to compositions and methods which yield a lower effective dose and/or less variable pharmacokinetic parameters (such as Tmax values with reduced variation) in comparison to conventional exogenous SAMe formulations or other SAMe formulations that lack a gallic acid ester ("SAMe control"). A "lower effective dose" or "reduced effective dose" is meant to define a physiologically acceptable dose of exogenous SAMe which results in pharmacokinetic parameters which are equivalent (or better) to a significantly higher dose of another SAMe formulation, such as that obtained through administration of a higher dose of one or more commercially available or "control" SAMe formulations. Formulations such as those provided herein which exhibit similar Cmax and AUC values at lower SAMe doses would have many benefits including a lower pill burden, increased rate of onset and/or potentially increased tolerability and/or compliance.

Additional embodiments also relate to compositions and methods which yield an improved side effect profile in comparison to conventional SAMe formulations. An "improved side effect" or "reduced side effect" or "beneficial side effect" profile is meant to define improved tolerability to administration of exogenous SAMe, such as less frequency and/or reduced intensity of side effects associated with SAMe supplementation. It is further recognized by the present investigators that any observed negative side effects associated with exogenous SAMe ion supplementation may be attributed to the SAMe counterion(s) present in the SAMe salts. By reducing the daily dose of exogenous SAMe ion needed to experience a positive therapeutic outcome, the corresponding significant reduction in SAMe counterion(s) may contribute to the improved side effect profile.

Some exemplary embodiments also relate to a dosing regimen of exogenous SAMe of once daily, or QD dosing, which results in improved pharmacokinetic profiles of SAMe in comparison to conventional twice daily or more frequent dosing. In certain embodiments, the effect of once a day dosing is believed to result in the most consistent pharmacokinetic parameter measurements, specifically those of the Cmax and Tmax. The less variable pharmacokinetic profiles that result from once a day dosing of formulations provided herein allow for more certainty of dosing and exposure by the medical practitioner as well as improved side effect profiles for subjects. Side effects include for example, nausea or stomach irritation, gastrointestinal upset, insomnia, headaches, irritation or possibly heart palpitations.

In some embodiments, formulations which exhibit superior pharmacokinetic profiles in comparison to conventional SAMe dosage forms, provide an improved rate of onset of SAMe which may result in enhanced therapeutic outcomes. Improved rate of onset is meant to mean the rate at which the subject experiences a positive outcome. For example, in Depression, the onset of antidepressant action is typically 4-6 weeks. SAMe formulations with improved pharmacokinetic profiles may be associated with corresponding improvement in therapeutic affect (e.g. antidepressant effect) in less than the typical or expected 4-6 weeks.

Other exemplary embodiments relate to methods for treating a disease or disorder in a subject and/or improving the nutritional status in a subject, said methods comprising administering to said subject compositions comprising physiologically effective dosages of exogenous SAMe in combination with one or more gallic acid ester thereby improving the pharmacokinetic profile of SAMe. Improved pharmacokinetic profiles are identified by, for example, an increase in Cmax and/or AUC values; or alternatively a decrease in effective dose; or pharmacokinetic parameters with reduced variation. Achieving one or more of these criteria would constitute an improvement in the pharmacokinetic profile of SAMe. Preferably, the gallic acid ester is propyl gallate.

In some embodiments, there is provided a method of treating or preventing a disease condition or disorder, comprising administering to a subject in need of such treatment an effective amount of a composition as described herein. In some embodiments, there is provided a method of treating in a patient a disease or disorder selected from the group consisting of mental and psychiatric disorders, nervous system diseases and disorders, neurological diseases and disorders, conditions associated with injuries to the central nervous system, liver diseases and disorders, cancers, joint diseases and disorders, inflammatory diseases and disorders, autoimmune diseases and disorders, degenerative diseases and disorders, soft-tissue diseases and disorders, pain diseases and disorders, cardiovascular disorders related to hyper-homocysteinemia and hypo-homocysteinemia, genetic disorders related to hyper-methylation and hypomethylation, gastrointestinal diseases and disorders, atherosclerosis, Lesch-Nyhan disease, and disorders induced in whole or in part by oxidative or free-radical damage, comprising administering to the patient in need thereof a composition as described herein. In some embodiments, the subject is human.

Excipients and Processing Parameters Suitable for Use in the Invention

The product or dosage form characteristics which result from the processing methods and/or parameters for generating formulations such as tablets, include, but are not limited to, hardness, thickness, water content, friability, disintegration, dissolution profile(s), shape, size, weight, uniformity and composition. These product characteristics can be modulated in a number of ways and affect the final in vitro and/or in vivo performance of the formulations. As an example, tablets generated by compression or molding processes may have varying degrees of thickness or hardness depending on the processing parameters under which they were made. Product or dosage form characteristics may be a consequence of excipient selection, excipient composition, manufacturing methods applied or a combination of any of these. The combination of excipients as well as product characteristics (including processing methods or processing parameters) of the final dosage form will ultimately determine the pharmacokinetic profile of the active ingredient in vivo. The SAMe formulations of the invention may be processed or manufactured under specific conditions such as, for example, mixing methods (including sieve size, rpm, and milling), drying time, press conditions, environmental parameters (e.g. temperature and humidity) and combinations thereof. In order to quantitatively compare one tablet to another, it is customary to measure several of these product or dosage form characteristics. This is also necessary when attempting to duplicate multiple batches.

Excipients are usually grouped by their function such as: disintegrants, diluents, binders, lubricants, glidants, coatings, coloring agents or flavoring agents, and the same excipient may be used for more than one function in a given oral formulation. Commonly used pharmaceutically acceptable excipients include water, magnesium stearate, starch, lactose, microcrystalline cellulose, stearic acid, sucrose, talc, silicon dioxide, gelatin, acacia and dibasic calcium phosphate (Baldrick, P. (2000) *Regul. Toxicol. Pharmacol. October* 32(2):210.) Excipients are combined with active ingredients for example to enhance appearance, improve stability, aid processing or aid disintegration after administration, but many other excipient functions are known in the art that can be applied to SAMe oral dosage forms. Classes of excipients which are often used and suitable for use in the present invention include but are not limited to, natural, modified-natural or synthetic mono-, oligo- or polysaccharides where oligo- and polysaccharides may or may not be physically or chemically crosslinked; natural, modified-natural or synthetic mono-, oligo- and polypeptides or proteins where oligo- and polypeptides and proteins may or may not be physically or chemically crosslinked; synthetic oligomers and polymers that may or may not be physically or chemically crosslinked; monomeric, hydrophobic, hydrophilic or amphoteric organic molecules; inorganic salts or metals; and combinations thereof.

Disintegrants

Disintegrants are added to non-parenteral formulations to induce breakup of the product or dosage form (i.e. tablet or capsule) when it comes in contact with aqueous fluid in order to help release the drug. The objectives behind addition of disintegrants are to increase surface area of the product fragments and to overcome cohesive forces that keep these particles together in a formulation. They do this by promoting wetting and swelling of the dosage form so that it breaks up in the gastrointestinal tract. Some binders such as starch and cellulose also act as disintegrants. Other disintegrants are clays, cellulose derivatives, algins, gums and crosslinked polymers. Another group of disintegrants called "super-disintegrants" are often utilized. These materials are effective at low (2-5%) concentrations. "Super-disintegrants" which may be suitable for use in the present invention include, but are not limited to, sodium starch glycolate (SSG), croscarmellose sodium or crosprovidone.

In some embodiments, compositions provided herein comprise SAMe and one or more gallic acid esters as well as one or more disintegrants or "super-disintegrants" which improve the pharmacokinetic profile of SAMe in vivo.

Binders

The binding material which holds the bulk of the product together and also helps maintain the product in a desired shape is known as a "binder" or "granulator". Binders suitable for use in the present invention are exemplified by, but are not limited to, sugars, gelatin, gums, microcrystalline cellulose and modified celluloses, waxes or synthetic polymers like polyethylene glycol or polyvinyl pyrrolidone. Some embodiments may include improved pharmacokinetic compositions comprising SAMe and one more gallic acid ester as well as one or more binders.

Lubricants

Additional excipients often utilized in product formulations are lubricants. These are substances which aid in the manufacturing process as they help minimize clumping of the products and also help release them from the manufacturing machinery. The most common "lubricant" used for oral formulations is magnesium stearate; however, other commonly used product lubricants include talc, calcium stearate, stearic acid (stearin), hydrogenated vegetable oils, sodium benzoate, leucine, carbowax 4000 and sodium stearyl fumarate all of which may be suitable for use in the present invention. Further exemplary embodiments also relate to improved pharmacokinetic compositions comprising SAMe and one or more gallic acid esters and one or more lubricants.

Glidants

Glidants also referred to as "flow-aids", help to keep the powder making up the products flowing as the products are being made, stopping them from forming lumps. Examples of commonly used glidants which may be suitable for use in the invention include colloidal silicon dioxide, talc, calcium silicate and magnesium silicate. Additional embodiments relate to improved pharmacokinetic compositions comprising SAMe and one or more gallic acid esters and one or more glidants.

The suitability of a particular excipient, such as, for example, a "matrix material", "disintegrant", "super-disintegrant" "binder", "lubricant", "glidant", or "coating" may be identified by analyzing the in vivo pharmacokinetics of formulations containing the excipient, gallic acid ester and SAMe. Alternatively, in vitro analysis of one or more excipients using a series of standard in vitro techniques which are well known in the art may be used to pre-screen excipients and ultimately provide a means to predict in vivo pharmacokinetic profiles. Furthermore, the use of references in the art may also provide insight into potentially suitable pharmaceutically or nutritionally acceptable excipients (such as a "matrix material", "disintegrant", "binder", "lubricant", "glidant", or "coating") for use in the present invention. Preferably, in vitro analysis of one or more excipients using dissolution studies conducted with a buffer pH of 6.8 or less may be used to pre-screen excipients and ultimately provide a means to predict in vivo pharmacokinetic profiles.

Processing Methods and Parameters

Processing methods and/or parameters which may be modified in order to improve the pharmacokinetic profile and/or alter the dissolution profile of SAMe-gallic acid ester formulations include but are not limited to: relative humidity, temperature, drying time and other environmental parameters.

The present embodiments are further described by the following examples. These examples, while illustrating certain specific aspects of the present embodiments, should not be considered to limit or circumscribe the scope of the disclosed embodiments.

EXAMPLES

Example 1

Propyl Gallate Significantly Increases Plasma Levels of Exogenously Administered SAMe Tablets comprising SAMe and various alkyl gallates of different chemical structure were generated by mixing SAMe with either methyl gallate, ethyl gallate, butyl gallate, isobutyl gallate, isoamyl gallate or octyl gallate (see structures below). Tablets were then administered to Beagle dogs and blood samples were withdrawn over time. Analysis of concentrations of SAMe in plasma was used to compare the effects of these gallic acid esters on the uptake of orally administered SAMe in the blood.

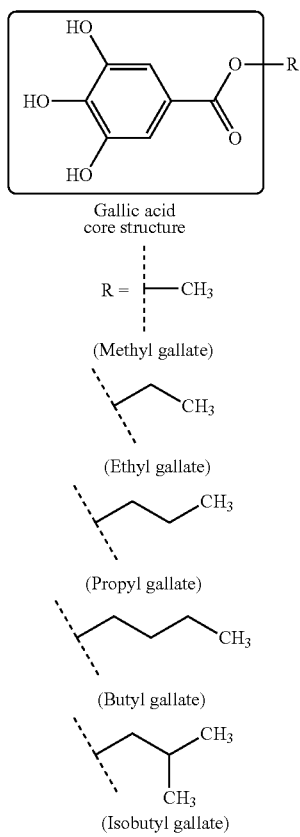

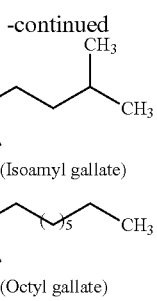

Tablets were generated by mixing 400 mg SAMe ion (from SAMe disulfate tosylate) with 25 mg gallic acid ester along with excipients (microcrystalline cellulose, sodium starch glycolate, silicon dioxide, and magnesium stearate) to make up the ~1025 mg tablet. A commercial seal coat and then a commercial enteric coat was applied to the tablets prior to dissolution testing. Detailed dissolution profiling was performed according to USP standards at either pH 6.8 or 6.0 on each set of tablets to ensure that adequate dissolution was achieved prior to in vivo pharmacokinetic analysis.

For in vivo studies, fasted male beagle dogs (7-10 kg) were used. The study protocol was approved by the institution's Animal Care Committee, and all animals were cared for according to regulations proposed by Agriculture Canada and the USDA. Each group (consisting of 6 dogs) was dosed with a single orally administered enteric coated tablet, under fasted conditions, followed by 5 mL of purified water orally with a syringe to facilitate swallowing. Blood samples (2 mL each) for SAMe analysis were collected from the jugular vein using the following time points: pre-dose, 20 and 40 minutes, 1, 1.5, 2, 3, 4, 6, and 8 hours after treatment. The venipuncture blood samples were collected into tubes containing the anticoagulant K2-EDTA, and stored on wet ice pending processing. Following collection, samples were centrifuged (at 4° C.) to separate the plasma fraction from the blood cells. The resulting plasma fraction was recovered and stored frozen (at −80° C.) using polypropylene tubes pending bioanalytical analysis.

The concentration of SAMe in dog plasma was determined using a well established liquid chromatography-tandem mass spectrometry (LC/MS/MS) method. This method employs stable-isotope dilution liquid chromatography-electrospray injection tandem mass spectrometry (LC-ESI-MS/MS) to determine SAMe and SAH in plasma. The analysis used to calculate the main pharmacokinetic parameters (Cmax, Tmax and AUC) was conducted using GraphPad Prism® 5 software.

Ten different formulations were tested in the present study. 400 mg SAMe co-formulated with 25 mg propyl gallate was compared to: SAMe control tablets (i.e., with no propyl gallate); SAMe tablets co-administered with separate 25 mg propyl gallate tablets; a commercially available SAMe product (400 mg); or 400 mg SAMe with 25 mg of either methyl gallate, ethyl gallate, butyl gallate, isobutyl gallate, isoamyl gallate or octyl gallate.

The graph in FIG. 1 clearly shows the superior combination of SAMe and ethyl gallate, propyl gallate, isoamyl gallate or octyl gallate. The maximum SAMe plasma concentration of these 10 formulations identifies for the first time that SAMe co-formulated with either ethyl gallate, propyl gallate, isoamyl gallate or octyl gallate has superior uptake into the plasma as compared to the other gallic acid ester formulations tested. Surprisingly, administration of SAMe with alkyl gallates whose alkyl moiety differs by as little as one carbon (e.g. butyl gallate) did not result in pharmacokinetics even close to that of SAMe-propyl gallate formulations.

Example 2

Beagle Plasma SAMe Levels in the Presence of Gallate-Related Molecules

In vivo experiments similar to those conducted in Example 1 were also performed using SAMe compositions comprising butylated hydroxytoluene (BHT), propyl paraben or gallic acid, all of which are agents that are well-known to be structurally similar to propyl gallate. BHT, propyl paraben and propyl gallate are food-grade antioxidants which have often been used in combination. These agents are structurally similar as seen here:

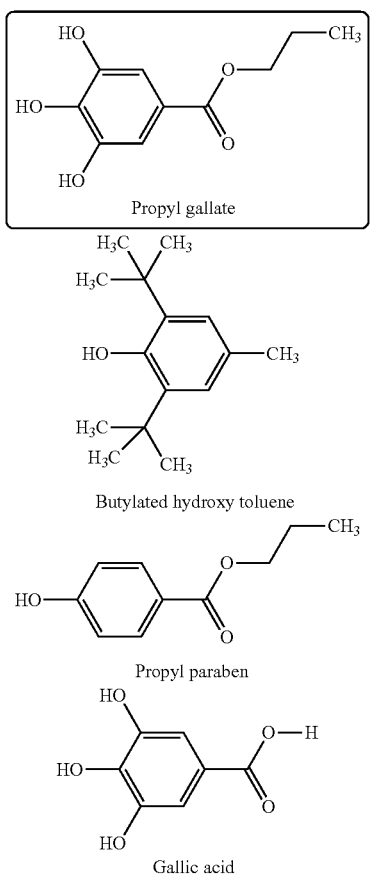

Capsules comprising 100 mg of either butylated hydroxytoluene, propyl paraben, gallic acid or propyl gallate were formulated using size #000 gelatin capsules, each containing 100 mg of SAMe ion. The capsules also contained additional excipients (Microcrystalline cellulose, Sodium Starch Glycolate, Colloidal Silicon Dioxide, and Magnesium Stearate). Capsules were manually filled and in some embodiments, a layer of commercial seal coat was applied to the capsules using a fluid bed coater.

Beagle dogs were administered a single orally delivered dose as described above. SAMe control capsules contained 100 mg of SAMe ion and no propyl gallate.

Figure 2A:
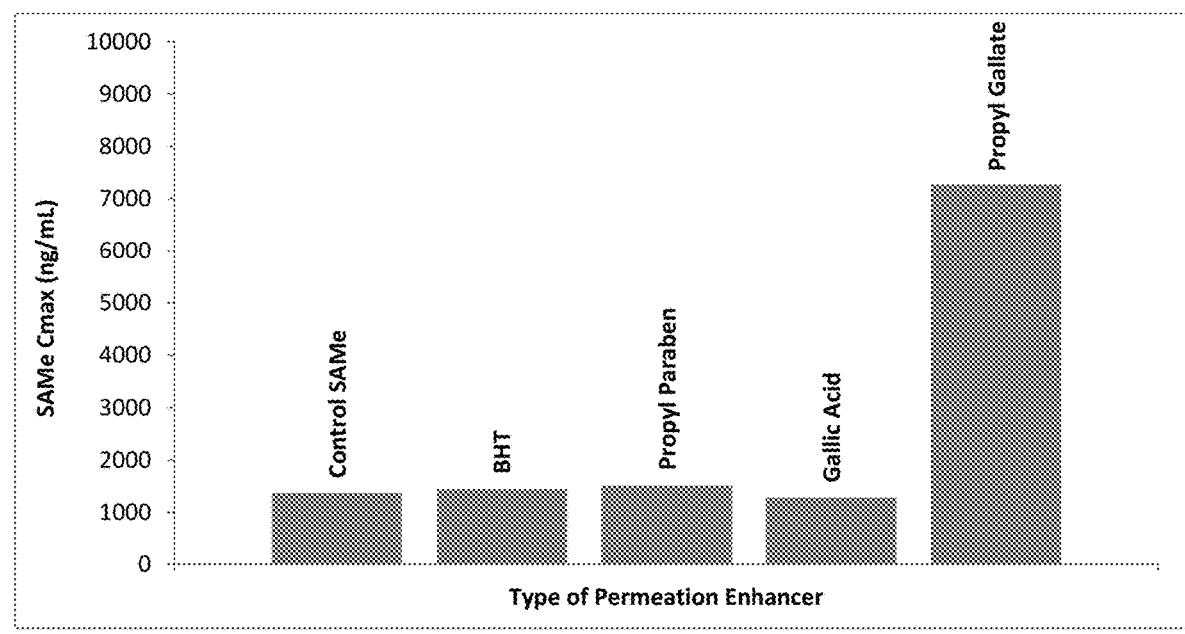
FIG. 2A is a graph showing the average maximum SAMe plasma concentration (Cmax) of beagles administered a single capsule containing 100 mg SAMe ion alone ("Control SAMe") or co-formulated with 100 mg of one of the following: butylated hydroxytoluene ("BHT"), propyl paraben or gallic acid.
Figure 2B:
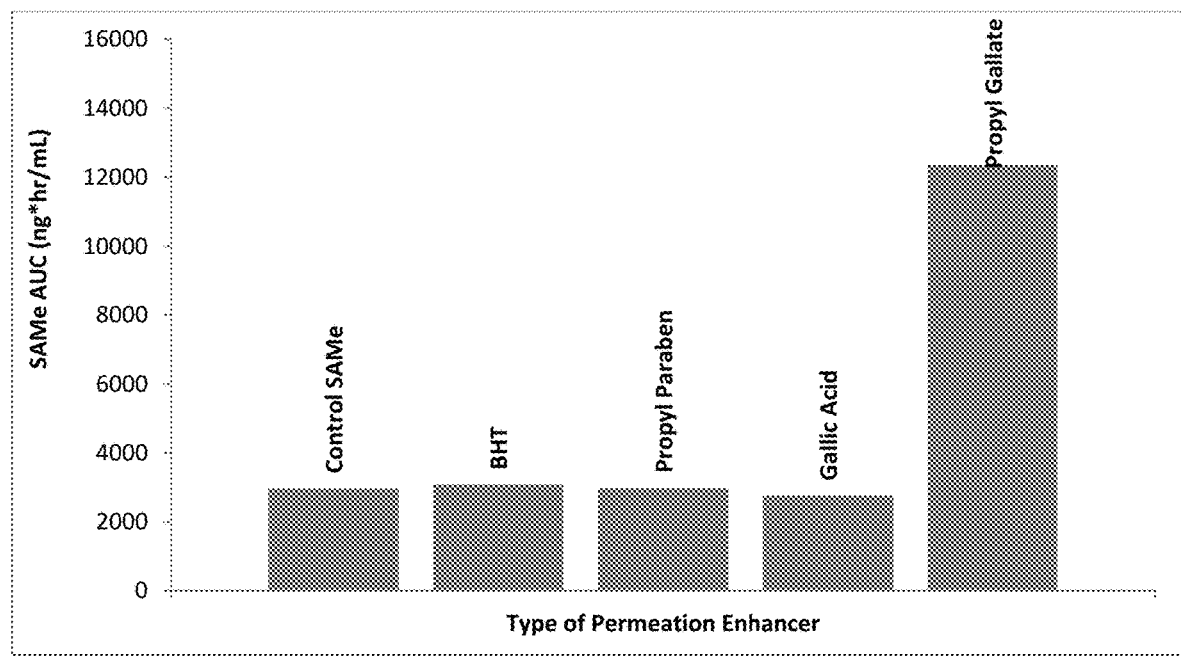
FIG. 2B is a graph showing the average SAMe plasma area under the curve (AUC) of beagles administered a single capsule containing 100 mg SAMe ion alone ("Control SAMe") or co-formulated with 100 mg of one of the following: butylated hydroxytoluene ("BHT"), propyl paraben or gallic acid.

The graphs in FIGS. 2A and 2B show the plasma SAMe Cmax and AUC, respectively, from each formulation and clearly present the superior and surprising ability of propyl gallate to increase SAMe uptake into the blood in comparison to the structurally similar butylated hydroxytoluene (BHT), propyl paraben and gallic acid.

Example 3

Effects of Propyl Gallate Dose on SAMe Uptake in Caco-2 Cell Transport

In vitro experiments on permeability of SAMe across Caco-2 cell monolayers treated with propyl gallate were conducted to identify levels of propyl gallate which increase the amount of SAMe absorbed by the Caco-2 cells in comparison to untreated Caco-2 cell monolayers. The Caco-2 cell line is derived from a human colorectal carcinoma and is widely used for in vitro cell culture models for the study of gastrointestinal drug absorption (Stewart, B., (1995) *Pharm. Res.* 12:693). In these models, pure cell lines are grown on a semi-permeable membrane. Drug formulations are placed on the apical or basolateral side of the cell monolayer and transport is determined via measurement of drug concentrations on the other side of the membrane.

The Caco-2 cell line utilized here was from the American Type Culture Collection (ATCC). Caco-2 cells are grown in Dulbecco's modified Eagle's medium (DMEM, Gibco) supplemented with 20% FBS (fetal bovine serum, Gibco), 100 uM non-essential amino acids (NEAA, Gibco) and 2 mM L-glutamine (Gibco). A Beckton Dickinson BIO-COAT® HTS Caco-2 Assay System Kit was used resulting in $6.6 \times 10^5$ cells/cm$^2$ seeding density (BIOCOAT is a registered trademark of Collaborative Biomedical Products, Inc., Bedford, Massachusetts, USA). The cells used in transport studies were grown for 3 days before the experiments. The culturing conditions were 37° C. in an atmosphere of 5% $CO_2$ and 100% humidity.

For permeability across Caco-2 cell monolayers, the transport medium used was Hank's Buffered Salt Solution (BBSS; purchased from Gibco) containing D-glucose, and HEPES pH adjusted to 7.4. A 2 mM aqueous solution of SAMe disulfate tosylate was added on the apical or basolateral side according to the manufacturer's procedure for the Caco-2 kit. Samples were measured after a 120-minute incubation by liquid chromatography-mass spectrometry (LC/MS). The integrity of the monolayers was monitored using Lucifer Yellow Assay.

The permeability (Papp) of SAMe is calculated using the following formula:

$$Papp = \frac{\frac{dQ}{dt}}{CoA}$$

Where dQ/dt is the rate of permeation, Co is the initial concentration of test agent, and A is the area of the monolayer.

SAMe absorption in Caco-2 cells was measured for two commonly used SAMe salts. The absorption was low for both SAMe salts (SAMe disulfate tosylate; SAMe 1,4 butanedisulfonate) as evidenced by a low apparent permeability coefficients (Papp=$0.41 \times 10^{-6}$ and $0.50 \times 10^{-6}$ cm s$^{-1}$, respectively, in apical to basolateral and basolateral to apical directions, respectively for SAMe disulfate tosylate; and Papp=$0.50 \times 10^{-6}$ and $0.60 \times 10^{-6}$ cm s$^{-1}$ in apical to basolateral and basolateral to apical directions, respectively for SAMe 1,4 butanedisulfonate. The results in Table 1 below show the absorption of SAMe disulfate tosylate in the presence of various concentrations of propyl gallate.

TABLE 1

Permeability of SAMe in the Presence of Propyl Gallate (Caco-2 Cell Model)

| Test Article | Excipient | Average Permeability Coefficient ($\times 10^{-4}$ cm/s) Apical→ Basolateral | Average Permeability Coefficient ($\times 10^{-4}$ cm/s) Basolateral→ Apical | Average TEER Resistance 19-hr post assay (ohms) |
|---|---|---|---|---|
| SAMe 2 mM | Propyl Gallate 0 mM | 0.016 | 0.017 | 6200 |
| SAMe 2 mM | Propyl Gallate 0.2 mM | 0.016 | Not determined | 5350 |
| SAMe 2 mM | Propyl Gallate 2 mM | 0.43 | Not determined | 3250 |

As shown in Table 1, propyl gallate increases SAMe transport in Caco-2 cells with good TEER recovery at the increased concentration.

Example 4

Effects of Propyl Gallate on SAMe Transport Using the PAMPA Model

Using a PAMPA (parallel artificial membrane permeability assay) model, the permeability of SAMe was measured in the presence and absence of propyl gallate. PAMPA models have been developed to exhibit a high degree of correlation with permeation across a variety of barriers, including the gastrointestinal tract. They are important here because these membranes do not comprise tight junctions, in contrast to the Caco-2 cell monolayer, and thus do not allow for paracellular transport.

PAMPA methods were used to determine the permeability of substances from a donor compartment, through a lipid-infused artificial membrane into an acceptor compartment. A multi-well microtitre plate was used for the donor and a membrane/acceptor compartment is placed on top. At the beginning of the test, SAMe disulfate tosylate (with or without different concentrations of propyl gallate as indicated in Table 2 below) was added to the donor compartment, and the acceptor compartment remained drug-free. After an incubation period, the compartments were separated and the amount of SAMe was measured in each compartment. Mass balance allows calculation of SAMe that remains in the membrane.

As seen in Table 2, SAMe showed essentially no transport across the PAMPA membrane and the presence of propyl gallate at 2.0 mM had no effect on SAMe transport. This is opposite to the effect of propyl gallate on SAMe using the Caco-2 cell transport model.

The artificial PAMPA membrane is a non-cellular lipid bilayer configured as a barrier, and experiments involving PAMPAs measure passive transport of molecules across this barrier, from one side to another. The fact that propyl gallate does not enhance permeability of SAMe across the PAMPA membrane means that the mechanism of enhancement is not through passive intracellular transport. The mechanism is therefore more likely to involve cellular components missing from the PAMPA model, such as tight junctions or active transport. Involvement of active transport via cell-based transporters was not supported by the Caco-2 cell model which showed that SAMe permeability from Apical to Basolateral was identical to permeability from Basolateral to Apical (see Table 1). Since epithelial cell transporter expression is typically localized to one direction or the other, the lack of a favored direction for permeability argues against intracellular active transport. That data is, however, consistent with a paracellular (tight junction) based mechanism of SAMe transport.

The fact that propyl gallate does not enhance the transport of other drugs known to be transported paracellularly (e.g. metformin or ranitidine—see Example 5 below) implies that the interaction of propyl gallate and SAMe is specific. Without being bound by any particular theory, based on the data, propyl gallate enhances the absorption of SAMe in a specific fashion with the route of transport involving tight junctions.

TABLE 2

Permeability of SAMe in the Presence of Propyl Gallate

| Test Article | Excipient | Average Effective Permeability ($\times 10^{-4}$ cm/s) | Assay Duration (hr) | % Recovery |
|---|---|---|---|---|
| SAMe 2 mM | Propyl Gallate 0 mM | 0.0042 | 5 | 114 |
| SAMe 2 mM | Propyl Gallate 0.2 mM | 0.0020 | 5 | 116 |
| SAMe 2 mM | Propyl Gallate 2 mM | 0.0048 | 5 | 116 |

Example 5

Effects of Propyl Gallate on the In Vitro Transport of Ranitidine and Metformin

Experiments similar to those conducted in Example 3 above were also performed using propyl gallate and either Ranitidine or Metformin, both of which have known paracellular intestinal transport mechanisms (Bourdet and Thakker, Pharm. Res. (2006) June; 23(6):1165-77 and Proctor, W. R. et al., Drug. Metab. Dispos. (2008) August; 36(8):1650-8).

For permeability across Caco-2 cell monolayers, the transport medium used was also Hank's Buffered Salt Solution (HBSS; purchased from Gibco) containing D-glucose, and HEPES pH adjusted to 7.4. Aqueous solutions of ranitidine or metformin (2 mM) containing 0 mM, 0.2 mM or 2.0 mM propyl gallate were added on the apical or basolateral side according to the manufacturer's procedure for the Caco-2 kit. Samples were measured after a 120 minute incubation using liquid chromatography-mass spectrometry (LC/MS). The integrity of the monolayers was monitored using Lucifer Yellow Assay.

As shown in Table 3 below, the presence of propyl gallate did not increase the rate of transport across the Caco-2 cell monolayer for either ranitidine or metformin, as it did with SAMe tosylate.

TABLE 3

Permeability of Ranitidine and Metformin in the Presence of Propyl Gallate

| Test Article | Test Concentration (µM) | Assay Duration (hr) | Average Effective Permeability ($\times 10^{-6}$ cm/s) |
|---|---|---|---|
| Metformin (2.0 mM) | 2000 | 2 | 0.18 |
| Metformin (2.0 mM) + propyl gallate (0.2 mM) | 2000 | 2 | 0.22 |

TABLE 3-continued

Permeability of Ranitidine and
Metformin in the Presence of Propyl Gallate

| Test Article | Test Concentration (μM) | Assay Duration (hr) | Average Effective Permeability ($\times 10^{-6}$ cm/s) |
|---|---|---|---|
| Metformin (2.0 mM) + propyl gallate (2.0 mM) | 2000 | 2 | 0.26 |
| Ranitidine (2.0 mM) | 2000 | 2 | 0.34 |
| Ranitidine (2.0 mM) + propyl gallate (0.2 mM) | 2000 | 2 | 0.28 |
| Ranitidine (2.0 mM) + propyl gallate (2.0 mM) | 2000 | 2 | 0.25 |

Example 6

Beagle Plasma SAMe Levels are Increased in the Presence of Various Doses of Propyl Gallate Tablets comprising SAMe and various amounts of propyl gallate were generated by mixing S-adenosyl-L-methionine disulfate tosylate granules (equivalent to 400 mg of SAMe ion) with the various amounts of propyl gallate listed in Table 4 below. Each mixture was pressed into a tablet and coated followed by dissolution profiling and in vivo pharmacokinetic analysis using beagle dogs.

Dissolution profiling was performed according to USP standards with either pH 6.0 or pH 6.8 buffers to ensure adequate tablet dissolution prior to administration to dogs.

The dissolution test method used is typically as follows:
USP Apparatus II operated at 100 RPM,
Fluid Phase: 1 L USP Simulated Gastric Fluid without enzyme, pH 1.2, 37° C.,
Aqueous Buffer Phase—1 L USP simulated Intestinal Fluid without enzyme, pH 6.8 or pH 6.0, 37° C.,
Tablets are exposed to the acid phase for two hours then transferred to the Buffer Phase,
Aliquots are drawn following exposure to the acid phase for 2 hours, then at prescribed intervals while in the buffer phase,
Samples are diluted 1→10 with n/10 HCL, and
Drug concentration is determined spectrophotometrically at 258 mm.

For in vivo studies, fasted male beagle dogs (7-10 kg) were used as described above. Each group (6 dogs for SAMe/propyl gallate and 6 dogs for the SAMe control lacking propyl gallate) were dosed with a single orally administered enteric coated tablet, under fasted conditions, followed by 5 mL of purified water orally with a syringe to facilitate swallowing. Pharmacokinetic blood samples (2 mL each) for SAMe analysis were collected from the jugular vein using the following time points: pre-dose, 20 and 40 minutes, 1, 1.5, 2, 3, 4, 6, and 8 hours after treatment. The venipuncture blood samples were collected into tubes containing the anticoagulant K2-EDTA, and stored on wet ice pending processing. Following collection, samples were centrifuged (at 4° C.) to separate the plasma fraction from the blood cells. The resulting plasma fraction was recovered and stored frozen (at −80° C.) using polypropylene tubes pending bioanalytical analysis.

The concentration of SAMe in dog plasma was determined using the well established LC/MS/MS method. This method employs stable-isotope dilution liquid chromatography-electrospray injection tandem mass spectrometry (LC-ESI-MS/MS) to determine SAMe and SAH in plasma. The analysis used to calculate the main pharmacokinetic parameters (Cmax, Tmax and AUC) was conducted using GraphPad Prism® 5 software.

As seen in Table 4 below, the maximum SAMe plasma concentration (Cmax) and AUC levels were significantly higher in formulations comprising all levels of propyl gallate in comparison to the control tablets of the SAMe salt alone. Surprisingly, the SAMe plasma concentration levels were also significantly higher when 400 mg SAMe ion was combined with as little as 6.25 mg of propyl gallate representing a 1:64 weight ratio of propyl gallate to SAMe.

TABLE 4

Tablets comprising SAMe plus decreasing amounts of propyl gallate

| SAMe Dose, mg | Propyl Gallate, mg | $T_{max}$ ± SD, hrs | Cmax average of individuals, ng/mL | $AUC_{(0-t)}$, hr*ng/mL | $AUC_{(0-inf)}$ ± SD, hr*ng/mL | $T_{1/2}$ ± SD, hrs |
|---|---|---|---|---|---|---|
| 400 | 100 | 1.6 ± 0.7 | 18,700 | 34,078 | 34,305 ± 18,484 | 1.0 ± 0.2 |
| 400 | 25 | 1.2 ± 0.5 | 15,333 | 24,847 | 25,159 ± 13,033 | 1.5 ± 0.4 |
| 400 | 0 | 1.8 ± 0.7 | 6731 | 14,756 | 15,186 ± 6,831 | 1.4 ± 0.4 |
| 400 | 6.25 | 1.4 ± 0.8 | 11,269 | 21,395 | 21,734 ± 9848 | 1.4 ± 0.5 |

These results demonstrate the surprising and dramatic increase in SAMe uptake in the presence of minimal amounts of propyl gallate.

Example 7

Propyl Gallate Significantly Increases Human Plasma Levels of Exogenous SAMe

A Phase I clinical study was carried out using tablets comprising SAMe and propyl gallate. Dose escalation of SAMe from 400 mg to 1600 mg was conducted using healthy, human volunteers. These SAMe-propyl gallate formulations were compared to one of the most commonly used commercially available SAMe products on the market which has been extensively studied in other SAMe clinical trials.

1025 mg tablets were generated by mixing 400 mg SAMe ion with 25 mg propyl gallate along with excipients to make up the 1025 mg (microcrystalline cellulose, sodium starch glycolate, silicon dioxide, and magnesium stearate). A seal coat and then enteric coat was applied to the tablets prior to dissolution testing and administration to human subjects—the exemplary formulation is referred to as the "MSI Formulation". These tablets comprising SAMe and propyl gallate had significantly higher Cmax and AUC values compared to the commercial product.

Table 5 show the plasma Cmax and AUC values for patients treated with 400 mg, 800 mg or 1600 mg of the MSI Formulation.

TABLE 5

Comparison of 400 mg, 800 mg and
1600 mg of SAMe ion in MSI Formulation

|  | MSI Formulation @ 400 mg SAMe ion[1] | MSI Formulation @ 800 mg SAMe ion | MSI Formulation @ 1600 mg[2] SAMe ion |
|---|---|---|---|
| Cmax, ng/mL | 1045 | 3255 | 4809 |
| AUC, ng hrs/mL | 4644 | 9361 | 16511 |
| Tmax, hrs | 7.75 | 3.0 | 3.25 |

[1] Using 6 evaluable subjects;
[2] Using 7 evaluable subjects

Figure 3A:
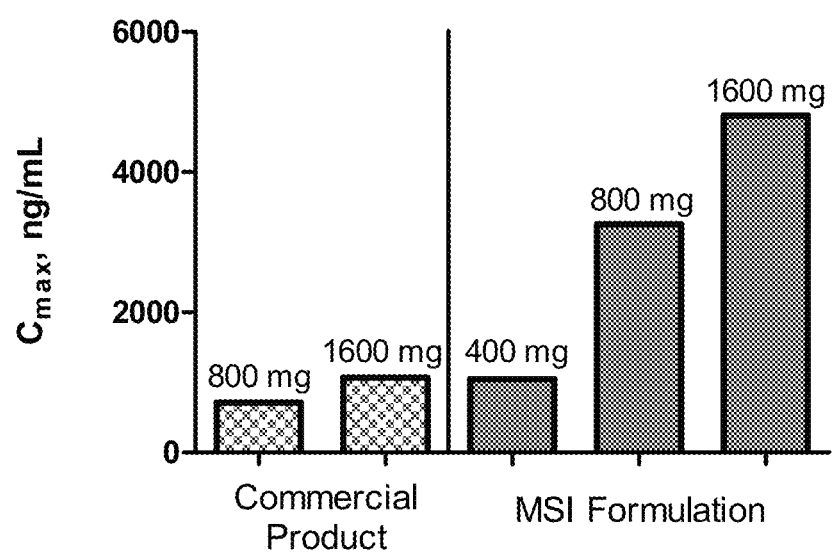
FIG. 3A is a graph showing the average maximum SAMe plasma concentration (Cmax) of human subjects administered a single dose of either 400 mg, 800 mg or 1600 mg of the MSI Formulation (SAMe and propyl gallate) or a 1600 mg dose of the commercial SAMe product.
Figure 3B:
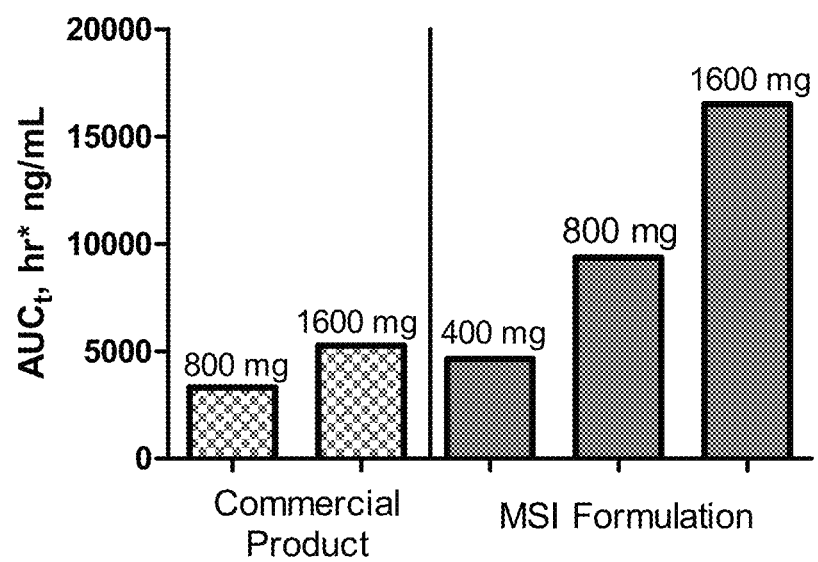
FIG. 3B is a graph showing the average SAMe plasma area under the curve (AUC) of human subjects administered a single dose of either 400 mg, 800 mg or 1600 mg of the MSI Formulation (SAMe and propyl gallate) or a 1600 mg dose of the commercial SAMe product.

The human plasma Cmax and AUC values of 400, 800 and 1600 mg of the MSI Formulation doses are graphed in comparison to the 800 and 1600 mg dose of the commercially available SAMe product which does not contain propyl gallate. As seen in both FIGS. 3A and 3B, at both 400 mg and 1600 mg dosages, the Cmax and AUC values of the MSI Formulation were significantly higher than those of the commercially available SAMe product. Also, the 400 mg dose of the MSI Formulation (containing SAMe and propyl gallate) achieved results comparable to a 1600 mg dose of the commercial product. Thus, lower dosages of SAMe-propyl gallate formulations are needed to achieve equivalent pharmacokinetics of the commercially available SAMe products.

These results further demonstrate the unexpected and significant benefits of using even low doses of propyl gallate in SAMe formulations.

Example 8

Gender Effect Evaluation of SAMe Compositions

There are multiple effects from administration of exogenous SAMe and many are known to be gender specific. There are various other theories to explain the gender difference in exogenous SAMe pharmacokinetics including larger body size and blood volume of males in general; higher body mass index (BMI) and different methylation states between the two sexes as well as the presence of particular genetic polymorphisms.

In order to assess the effects of gender on the MSI Formulation, a Phase I clinical study was carried out using tablets comprising SAMe and propyl gallate. 800 mg was administered to healthy, human volunteers (7 male, 17 female) as described above. The pharmacokinetic profile of these SAMe-propyl gallate formulations was also compared to the control commercial product as above.

1025 mg tablets were generated by mixing 400 mg SAMe ion with 25 mg propyl gallate along with excipients to make up the 1025 mg (microcrystalline cellulose, sodium starch glycolate, silicon dioxide, and magnesium stearate). A seal coat and then enteric coat was applied to the tablets prior to dissolution testing and administration to human subjects—the exemplary formulation is referred to as the "MSI Formulation". These tablets comprising SAMe and propyl gallate had significantly higher Cmax values compared to the commercial product.

The average maximum SAMe plasma concentration (Cmax) for male and female subjects treated with 800 mg of the MSI Formulation was 3832±927 ng/mL and 3054±580 ng/mL respectively (Average Cmax±Standard Error). Surprisingly, the MSI Formulation showed no significant difference in values between the two groups indicating that the MSI Formulation is able to overcome the known gender differences in SAMe pharmacokinetic values and thus significantly increase the SAME plasma levels equally well in both males and females.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a disease or disorder comprising administering a composition comprising an effective amount of exogenous S-adenosylmethionine (SAMe) and an effective amount of at least one gallic acid ester to a patient in need thereof,
    wherein the composition is formulated as an oral dosage form,
    wherein the disease or disorder is selected from the group consisting of depression, Alzheimer's disease, dementia, a liver disease or disorder, a cancer, an inflammatory disease or disorder, and atherosclerosis, and
    wherein the at least one gallic acid ester is selected from the group consisting of methyl gallate, ethyl gallate, propyl gallate, butyl gallate, isobutyl gallate, amyl gallate, isoamyl gallate, hexyl gallate, isohexyl gallate, heptyl gallate, isoheptyl gallate, octyl gallate, and isooctyl gallate.

2. The method of claim 1, wherein the at least one gallic acid ester is selected from the group consisting of methyl gallate, ethyl gallate, propyl gallate, butyl gallate, isobutyl gallate, isoamyl gallate, and octyl gallate.

3. The method of claim 2, wherein the gallic acid ester is ethyl gallate, isoamyl gallate, propyl gallate, or octyl gallate.

4. The method of claim 3, wherein the gallic acid ester is propyl gallate.

5. The method of claim 1, wherein the ratio of gallic acid ester to SAMe is from 5:1 (w/w) to 1:400 (w/w).

6. The method of claim 4, wherein the ratio of gallic acid ester to SAMe is from 5:1 (w/w) to 1:400 (w/w).

7. The method of claim 6, wherein the ratio of gallic acid ester to SAMe is from 1:2 (w/w) to 1:80 (w/w).

8. The method of claim 1, wherein the amount of the SAMe is about 10 mg to about 3600 mg.

9. The method of claim 4, wherein the amount of the SAMe is about 10 mg to about 3600 mg.

10. The method of claim 1, wherein the amount of the at least one gallic acid ester is about 1 mg to about 400 mg.

11. The method of claim 4, wherein the amount of the at least one gallic acid ester is about 1 mg to about 400 mg.

12. The method of claim 1, wherein the oral dosage form is selected from the group consisting of a capsule, a tablet, a paste, a granule, a caplet, and a lozenge.

13. The method of claim 1, wherein the composition further comprises at least one excipient, the at least one excipient selected from the group consisting of disintegrants, diluents, binders, lubricants, glidants, coatings, coloring agents, flavoring agents, and any combination thereof.

14. The method of claim 1, wherein the disease or disorder is depression, Alzheimer's disease, dementia, or atherosclerosis.

* * * * *